United States Patent
Kahn et al.

(10) Patent No.: US 11,883,188 B1
(45) Date of Patent: Jan. 30, 2024

(54) SLEEP SURFACE SENSOR BASED SLEEP ANALYSIS SYSTEM

(71) Applicants: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US)

(72) Inventors: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 420 days.

(21) Appl. No.: 15/071,189

(22) Filed: Mar. 15, 2016

Related U.S. Application Data

(60) Provisional application No. 62/133,734, filed on Mar. 16, 2015.

(51) Int. Cl.
*A61B 5/00* (2006.01)
*A61B 5/11* (2006.01)

(52) U.S. Cl.
CPC .............. *A61B 5/4806* (2013.01); *A61B 5/11* (2013.01); *A61B 5/6892* (2013.01)

(58) Field of Classification Search
CPC ....... A61B 5/4806; A61B 5/6892; A61B 5/11; A61B 2562/16; A61B 262/0247–0261; A61B 5/024; A61B 5/0816; A61B 2562/0247; A61B 2562/0252; A61B 2562/0261
USPC ......................................................... 600/595
See application file for complete search history.

(56) References Cited

U.S. PATENT DOCUMENTS

| | | | |
|---|---|---|---|
| 2,082,843 | A | 6/1937 | Mathez |
| 3,541,781 | A | 11/1970 | Bloom |
| 3,683,933 | A | 8/1972 | Mansfield |
| 3,798,889 | A | 3/1974 | Chadwick |
| 4,228,806 | A | 10/1980 | Lidow |
| 4,297,685 | A | 10/1981 | Brainard, II |
| 4,322,609 | A | 3/1982 | Kato |
| 4,573,804 | A | 3/1986 | Kavoussi et al. |
| 4,788,533 | A | 11/1988 | Mequignon |
| 4,848,360 | A | 7/1989 | Palsgard et al. |

(Continued)

FOREIGN PATENT DOCUMENTS

| | | |
|---|---|---|
| AU | 2003203967 A1 | 11/2004 |
| CH | 377738 A | 1/1964 |

(Continued)

OTHER PUBLICATIONS

"NPL—EasySense LTD", archive.org, accessed: Jan. 7, 2019, published: Nov. 27, 2006.*

(Continued)

*Primary Examiner* — Daniel L Cerioni
(74) *Attorney, Agent, or Firm* — Nicholson De Vos Webster & Elliott LLP; Judith Szepesi

(57) ABSTRACT

A method comprising receiving data from a sleep sensor integrated in a mattress system, the sleep sensor coupled via a cord to a data collection unit, analyzing the data at the data collection unit, and providing results of the analyzed data to a user mobile device via a wireless connection, for display to the user.

21 Claims, 20 Drawing Sheets

(56) References Cited

U.S. PATENT DOCUMENTS

| | | | |
|---|---|---|---|
| 4,858,609 A | 8/1989 | Cole | |
| 4,982,738 A | 1/1991 | Griebel | |
| 5,008,865 A | 4/1991 | Shaffer et al. | |
| 5,047,930 A | 9/1991 | Martens et al. | |
| 5,168,759 A * | 12/1992 | Bowman | A61B 5/113 |
| | | | 29/595 |
| 5,275,159 A | 1/1994 | Griebel | |
| 5,335,657 A | 8/1994 | Terry, Jr. et al. | |
| 5,458,105 A | 10/1995 | Taylor et al. | |
| 5,545,192 A | 8/1996 | Czeisler et al. | |
| 5,562,106 A | 10/1996 | Heeke et al. | |
| 5,671,733 A | 9/1997 | Raviv et al. | |
| 5,844,996 A | 12/1998 | Enzmann et al. | |
| 5,868,647 A | 2/1999 | Belsole | |
| 5,928,133 A | 7/1999 | Halyak | |
| 5,961,447 A | 10/1999 | Raviv et al. | |
| 6,014,682 A | 1/2000 | Stephen et al. | |
| 6,045,514 A | 4/2000 | Raviv et al. | |
| 6,231,527 B1 * | 5/2001 | Sol | A61B 5/1038 |
| | | | 348/143 |
| 6,239,706 B1 | 5/2001 | Yoshiike et al. | |
| 6,350,275 B1 | 2/2002 | Vreman et al. | |
| 6,361,508 B1 | 3/2002 | Johnson et al. | |
| 6,468,234 B1 | 10/2002 | Van et al. | |
| 6,547,728 B1 | 4/2003 | Cornuejols | |
| 6,556,222 B1 | 4/2003 | Narayanaswami | |
| 6,834,436 B2 | 12/2004 | Townsend et al. | |
| 6,888,779 B2 | 5/2005 | Mollicone et al. | |
| 6,928,031 B1 | 8/2005 | Kanevsky et al. | |
| 6,963,271 B1 | 11/2005 | Fyffe | |
| 7,006,650 B1 | 2/2006 | Wild | |
| 7,041,049 B1 | 5/2006 | Raniere | |
| 7,106,662 B1 | 9/2006 | Acker, Jr. | |
| 7,139,342 B1 | 11/2006 | Phanse | |
| 7,153,278 B2 | 12/2006 | Ono et al. | |
| 7,280,439 B1 | 10/2007 | Shaddox | |
| 7,366,572 B2 | 4/2008 | Heruth et al. | |
| 7,513,003 B2 | 4/2009 | Mossbeck | |
| 7,559,903 B2 | 7/2009 | Moussavi et al. | |
| 7,572,225 B2 | 8/2009 | Stahmann et al. | |
| 7,652,581 B2 * | 1/2010 | Gentry | A61B 5/11 |
| | | | 340/573.1 |
| 7,841,987 B2 | 11/2010 | Sotos et al. | |
| 7,862,226 B2 | 1/2011 | Bracher et al. | |
| 7,868,757 B2 | 1/2011 | Radivojevic et al. | |
| 7,914,468 B2 | 3/2011 | Shalon et al. | |
| 7,974,849 B1 | 7/2011 | Begole et al. | |
| 8,179,270 B2 | 5/2012 | Rai et al. | |
| 8,193,941 B2 | 6/2012 | Wolfe et al. | |
| 8,398,546 B2 | 3/2013 | Pacione et al. | |
| 8,407,835 B1 | 4/2013 | Connor | |
| 8,475,339 B2 | 7/2013 | Hwang et al. | |
| 8,482,418 B1 | 7/2013 | Harman | |
| 8,577,448 B2 | 11/2013 | Bauer et al. | |
| 8,680,974 B2 | 3/2014 | Meiertoberens et al. | |
| 8,738,925 B1 | 5/2014 | Park et al. | |
| 8,892,036 B1 | 11/2014 | Causey et al. | |
| 8,909,357 B2 | 12/2014 | Rawls-Meehan | |
| 8,942,719 B1 | 1/2015 | Hyde et al. | |
| 9,060,735 B1 | 6/2015 | Yang et al. | |
| 9,161,719 B2 | 10/2015 | Tsutsumi et al. | |
| 9,257,029 B1 | 2/2016 | Hendrick, III et al. | |
| 9,448,536 B1 | 9/2016 | Kahn et al. | |
| 9,474,876 B1 | 10/2016 | Kahn et al. | |
| 9,594,354 B1 | 3/2017 | Kahn et al. | |
| 9,675,268 B2 | 6/2017 | Bauer et al. | |
| 9,844,336 B2 | 12/2017 | Zigel et al. | |
| 10,004,452 B2 | 6/2018 | Kazem-Moussavi et al. | |
| 10,207,075 B1 | 2/2019 | Kahn et al. | |
| 10,252,058 B1 | 4/2019 | Fuerst | |
| 10,335,060 B1 | 7/2019 | Kahn et al. | |
| 10,842,968 B1 | 11/2020 | Kahn et al. | |
| 11,100,922 B1 | 8/2021 | Mutagi et al. | |
| 2001/0049482 A1 | 12/2001 | Pozos et al. | |
| 2002/0080035 A1 | 6/2002 | Youdenko | |
| 2002/0100477 A1 | 8/2002 | Sullivan et al. | |
| 2002/0124848 A1 | 9/2002 | Sullivan et al. | |
| 2003/0095476 A1 | 5/2003 | Mollicone et al. | |
| 2003/0204412 A1 | 10/2003 | Brier | |
| 2003/0227439 A1 | 12/2003 | Lee et al. | |
| 2003/0231495 A1 | 12/2003 | Searfoss, III | |
| 2004/0034289 A1 | 2/2004 | Teller et al. | |
| 2004/0049132 A1 | 3/2004 | Barron et al. | |
| 2004/0071382 A1 | 4/2004 | Rich et al. | |
| 2004/0111039 A1 * | 6/2004 | Minamiura | A61B 5/0205 |
| | | | 600/513 |
| 2004/0133081 A1 | 7/2004 | Teller et al. | |
| 2004/0210155 A1 | 10/2004 | Takemura et al. | |
| 2004/0218472 A1 | 11/2004 | Narayanaswami et al. | |
| 2005/0012622 A1 | 1/2005 | Sutton | |
| 2005/0043645 A1 | 2/2005 | Ono et al. | |
| 2005/0075116 A1 | 4/2005 | Laird et al. | |
| 2005/0076715 A1 * | 4/2005 | Kuklis | A61B 5/11 |
| | | | 73/541 |
| 2005/0143617 A1 | 6/2005 | Auphan | |
| 2005/0154330 A1 | 7/2005 | Loree, IV | |
| 2005/0190065 A1 | 9/2005 | Ronnholm | |
| 2005/0236003 A1 | 10/2005 | Meader | |
| 2005/0237479 A1 | 10/2005 | Rose | |
| 2005/0245793 A1 | 11/2005 | Hilton et al. | |
| 2005/0283039 A1 | 12/2005 | Cornel | |
| 2005/0288904 A1 | 12/2005 | Warrior et al. | |
| 2006/0017560 A1 | 1/2006 | Albert | |
| 2006/0025299 A1 | 2/2006 | Miller et al. | |
| 2006/0064037 A1 | 3/2006 | Shalon et al. | |
| 2006/0097884 A1 | 5/2006 | Jang et al. | |
| 2006/0136018 A1 | 6/2006 | Lack et al. | |
| 2006/0150734 A1 | 7/2006 | Mimnagh-Kelleher et al. | |
| 2006/0252999 A1 | 11/2006 | Devaul et al. | |
| 2006/0266356 A1 | 11/2006 | Sotos et al. | |
| 2006/0279428 A1 | 12/2006 | Sato et al. | |
| 2006/0293602 A1 | 12/2006 | Clark | |
| 2006/0293608 A1 | 12/2006 | Rothman et al. | |
| 2007/0016091 A1 | 1/2007 | Butt et al. | |
| 2007/0016095 A1 | 1/2007 | Low et al. | |
| 2007/0093722 A1 | 4/2007 | Noda et al. | |
| 2007/0100666 A1 | 5/2007 | Stivoric et al. | |
| 2007/0129644 A1 | 6/2007 | Richards et al. | |
| 2007/0139362 A1 | 6/2007 | Colton et al. | |
| 2007/0191692 A1 | 8/2007 | Hsu et al. | |
| 2007/0239225 A1 | 10/2007 | Saringer | |
| 2007/0250286 A1 | 10/2007 | Duncan et al. | |
| 2007/0251997 A1 | 11/2007 | Brown et al. | |
| 2007/0287930 A1 | 12/2007 | Sutton | |
| 2008/0062818 A1 | 3/2008 | Plancon et al. | |
| 2008/0109965 A1 | 5/2008 | Mossbeck | |
| 2008/0125820 A1 | 5/2008 | Stahmann et al. | |
| 2008/0169931 A1 | 7/2008 | Gentry et al. | |
| 2008/0191885 A1 | 8/2008 | Loree, IV et al. | |
| 2008/0234785 A1 | 9/2008 | Nakayama et al. | |
| 2008/0243014 A1 | 10/2008 | Moussavi et al. | |
| 2008/0269625 A1 | 10/2008 | Halperin et al. | |
| 2008/0275348 A1 | 11/2008 | Catt et al. | |
| 2008/0275349 A1 | 11/2008 | Halperin et al. | |
| 2008/0289637 A1 | 11/2008 | Wyss | |
| 2008/0319277 A1 | 12/2008 | Bradley | |
| 2009/0030767 A1 | 1/2009 | Morris et al. | |
| 2009/0048540 A1 | 2/2009 | Otto et al. | |
| 2009/0069644 A1 | 3/2009 | Hsu et al. | |
| 2009/0071810 A1 * | 3/2009 | Hanson | A01K 1/126 |
| | | | 200/339 |
| 2009/0082699 A1 | 3/2009 | Bang et al. | |
| 2009/0094750 A1 | 4/2009 | Oguma et al. | |
| 2009/0105785 A1 | 4/2009 | Wei et al. | |
| 2009/0121826 A1 | 5/2009 | Song et al. | |
| 2009/0128487 A1 | 5/2009 | Langereis et al. | |
| 2009/0143636 A1 | 6/2009 | Mullen et al. | |
| 2009/0150217 A1 | 6/2009 | Luff | |
| 2009/0177327 A1 | 7/2009 | Turner et al. | |
| 2009/0203970 A1 | 8/2009 | Fukushima et al. | |
| 2009/0203972 A1 | 8/2009 | Heneghan et al. | |
| 2009/0207028 A1 | 8/2009 | Kubey et al. | |
| 2009/0227888 A1 | 9/2009 | Salmi et al. | |
| 2009/0264789 A1 | 10/2009 | Molnar et al. | |

(56) References Cited

U.S. PATENT DOCUMENTS

| | | |
|---|---|---|
| 2009/0320123 A1 | 12/2009 | Yu et al. |
| 2010/0010330 A1 | 1/2010 | Rankers et al. |
| 2010/0010565 A1 | 1/2010 | Lichtenstein et al. |
| 2010/0036211 A1* | 2/2010 | La Rue ............... A61B 5/0002 600/301 |
| 2010/0061596 A1 | 3/2010 | Mostafavi et al. |
| 2010/0075807 A1 | 3/2010 | Hwang et al. |
| 2010/0079291 A1 | 4/2010 | Kroll et al. |
| 2010/0079294 A1 | 4/2010 | Rai et al. |
| 2010/0083968 A1 | 4/2010 | Wondka et al. |
| 2010/0094139 A1* | 4/2010 | Brauers ............... A61B 5/024 600/484 |
| 2010/0094148 A1 | 4/2010 | Bauer et al. |
| 2010/0100004 A1 | 4/2010 | Van Someren |
| 2010/0102971 A1 | 4/2010 | Virtanen et al. |
| 2010/0152543 A1 | 6/2010 | Heneghan et al. |
| 2010/0152546 A1 | 6/2010 | Behan et al. |
| 2010/0217146 A1 | 8/2010 | Osvath |
| 2010/0256512 A1 | 10/2010 | Sullivan |
| 2010/0283618 A1 | 11/2010 | Wolfe et al. |
| 2010/0331145 A1 | 12/2010 | Lakovic et al. |
| 2011/0015467 A1 | 1/2011 | Dothie et al. |
| 2011/0015495 A1 | 1/2011 | Dothie et al. |
| 2011/0018720 A1 | 1/2011 | Rai et al. |
| 2011/0046498 A1 | 2/2011 | Klap et al. |
| 2011/0054279 A1 | 3/2011 | Reisfeld et al. |
| 2011/0058456 A1 | 3/2011 | Van et al. |
| 2011/0090226 A1 | 4/2011 | Sotos et al. |
| 2011/0105915 A1 | 5/2011 | Bauer et al. |
| 2011/0137836 A1 | 6/2011 | Kuriyama et al. |
| 2011/0160619 A1 | 6/2011 | Gabara |
| 2011/0190594 A1 | 8/2011 | Heit et al. |
| 2011/0199218 A1 | 8/2011 | Caldwell et al. |
| 2011/0230790 A1 | 9/2011 | Kozlov |
| 2011/0245633 A1 | 10/2011 | Goldberg et al. |
| 2011/0295083 A1 | 12/2011 | Doelling et al. |
| 2011/0302720 A1 | 12/2011 | Yakam et al. |
| 2011/0304240 A1 | 12/2011 | Meitav et al. |
| 2012/0004749 A1 | 1/2012 | Abeyratne et al. |
| 2012/0083715 A1 | 4/2012 | Yuen et al. |
| 2012/0232414 A1 | 9/2012 | Mollicone et al. |
| 2012/0243379 A1 | 9/2012 | Balli |
| 2012/0253220 A1 | 10/2012 | Rai et al. |
| 2012/0296156 A1 | 11/2012 | Auphan |
| 2013/0012836 A1 | 1/2013 | Crespo et al. |
| 2013/0018284 A1 | 1/2013 | Kahn et al. |
| 2013/0023214 A1 | 1/2013 | Wang et al. |
| 2013/0053653 A1 | 2/2013 | Cuddihy et al. |
| 2013/0053656 A1 | 2/2013 | Mollicone et al. |
| 2013/0060306 A1 | 3/2013 | Colbauch |
| 2013/0144190 A1 | 6/2013 | Bruce et al. |
| 2013/0184601 A1 | 7/2013 | Zigel et al. |
| 2013/0197857 A1 | 8/2013 | Lu et al. |
| 2013/0204314 A1 | 8/2013 | Miller, III et al. |
| 2013/0208576 A1 | 8/2013 | Loree, IV et al. |
| 2013/0283530 A1* | 10/2013 | Main ............... A47C 31/123 5/600 |
| 2013/0286793 A1 | 10/2013 | Umamoto |
| 2013/0289419 A1 | 10/2013 | Berezhnyy et al. |
| 2013/0300204 A1 | 11/2013 | Partovi |
| 2013/0310658 A1 | 11/2013 | Ricks et al. |
| 2013/0344465 A1 | 12/2013 | Dickinson et al. |
| 2014/0005502 A1 | 1/2014 | Klap et al. |
| 2014/0051938 A1 | 2/2014 | Goldstein et al. |
| 2014/0085077 A1 | 3/2014 | Luna et al. |
| 2014/0135955 A1 | 5/2014 | Burroughs |
| 2014/0171815 A1 | 6/2014 | Yang et al. |
| 2014/0200691 A1 | 7/2014 | Lee et al. |
| 2014/0207292 A1 | 7/2014 | Ramagem et al. |
| 2014/0218187 A1* | 8/2014 | Chun ............... G08B 21/06 340/439 |
| 2014/0219064 A1 | 8/2014 | Filipi et al. |
| 2014/0232558 A1 | 8/2014 | Park et al. |
| 2014/0256227 A1 | 9/2014 | Aoki et al. |
| 2014/0259417 A1 | 9/2014 | Nunn et al. |
| 2014/0259434 A1 | 9/2014 | Nunn et al. |
| 2014/0276227 A1 | 9/2014 | Perez |
| 2014/0288878 A1 | 9/2014 | Donaldson |
| 2014/0306833 A1 | 10/2014 | Ricci |
| 2014/0350351 A1 | 11/2014 | Halperin et al. |
| 2014/0371635 A1 | 12/2014 | Shinar et al. |
| 2015/0015399 A1* | 1/2015 | Gleckler ............... A61B 5/1116 340/573.7 |
| 2015/0068069 A1 | 3/2015 | Tran et al. |
| 2015/0073283 A1 | 3/2015 | Van et al. |
| 2015/0085622 A1 | 3/2015 | Carreel et al. |
| 2015/0094544 A1 | 4/2015 | Spolin et al. |
| 2015/0098309 A1 | 4/2015 | Adams et al. |
| 2015/0101870 A1 | 4/2015 | Gough et al. |
| 2015/0136146 A1 | 5/2015 | Hood et al. |
| 2015/0141852 A1 | 5/2015 | Dusanter et al. |
| 2015/0148621 A1 | 5/2015 | Sier |
| 2015/0148871 A1 | 5/2015 | Maxik et al. |
| 2015/0164238 A1 | 6/2015 | Benson et al. |
| 2015/0164409 A1 | 6/2015 | Benson et al. |
| 2015/0164438 A1* | 6/2015 | Halperin ............... G16H 50/20 340/573.1 |
| 2015/0173671 A1 | 6/2015 | Paalasmaa et al. |
| 2015/0178362 A1 | 6/2015 | Wheeler |
| 2015/0190086 A1 | 7/2015 | Chan et al. |
| 2015/0220883 A1 | 8/2015 | Lingg et al. |
| 2015/0233598 A1 | 8/2015 | Shikii et al. |
| 2015/0238139 A1 | 8/2015 | Raskin et al. |
| 2015/0265903 A1 | 9/2015 | Kolen et al. |
| 2015/0289802 A1 | 10/2015 | Thomas et al. |
| 2015/0320588 A1 | 11/2015 | Connor |
| 2015/0333950 A1 | 11/2015 | Johansson |
| 2015/0351694 A1* | 12/2015 | Shimizu ............... A61B 5/4806 600/508 |
| 2016/0015315 A1 | 1/2016 | Auphan et al. |
| 2016/0045035 A1* | 2/2016 | Van Erlach ............ A61B 5/0036 700/279 |
| 2016/0217672 A1 | 7/2016 | Yoon et al. |
| 2016/0262693 A1 | 9/2016 | Sheon |
| 2016/0287869 A1 | 10/2016 | Errico et al. |
| 2017/0003666 A1 | 1/2017 | Nunn et al. |
| 2017/0020756 A1* | 1/2017 | Hillenbrand, II .... A61B 5/6891 |
| 2017/0188938 A1 | 7/2017 | Toh et al. |
| 2018/0049701 A1* | 2/2018 | Raisanen ............... A61B 5/1102 |
| 2018/0103770 A1 | 4/2018 | Nava et al. |
| 2018/0338725 A1 | 11/2018 | Shan et al. |
| 2019/0021675 A1 | 1/2019 | Gehrke et al. |
| 2019/0044380 A1 | 2/2019 | Lausch et al. |
| 2019/0132570 A1 | 5/2019 | Chen et al. |
| 2019/0156296 A1 | 5/2019 | Lu et al. |
| 2019/0190992 A1 | 6/2019 | Warrick |
| 2019/0201270 A1 | 7/2019 | Sayadi et al. |

FOREIGN PATENT DOCUMENTS

| | | |
|---|---|---|
| CH | 668349 A | 12/1988 |
| CH | 697528 B1 | 11/2008 |
| DE | 19642316 A1 | 4/1998 |
| EP | 1139187 A2 | 10/2001 |
| JP | 08-160172 A | 6/1996 |
| JP | 2007-132581 A | 5/2007 |
| KR | 10-2009-0085403 A | 8/2009 |
| KR | 10-2010-0022217 A | 3/2010 |
| WO | 93/02731 A1 | 2/1993 |
| WO | 2008/038288 A2 | 4/2008 |
| WO | 2009/099292 A2 | 8/2009 |
| WO | 2011/141840 A1 | 11/2011 |

OTHER PUBLICATIONS

Acligraphy, From Wikipedia, the free encyclopedia, downloaded at: http://en.wikipedia.org/wiki/Actigraphy on Apr. 24, 2014, 4 pages.
Campbell, Appleinsider, "Apple buys sleep tracking firm Beddit" May 9, 2017. Retrieved from https://appleinsider.com/articles/May 17, 09/apple-buys-sleep-tracking-firm-beddit (Year: 2017).

(56) References Cited

OTHER PUBLICATIONS

Crist, CNET "Samsung introduces SleepSense" Sep. 3, 2015. Retrieved from https://www.cnet.com/reviews/samsung-sleepsense-preview (Year: 2015).

Daniel et al., "Activity Characterization from Actimetry Sensor Data for Sleep Disorders Diagnosis", Sep. 2008, 10 pages.

Desai, Rajiv, "The Sleep", Mar. 17, 2011, Educational Blog, 82 pages.

Fitbit Product Manual, "Fitbit Product Manual", available online at <http://www.filtbit.com/manual>, Mar. 29, 2010, pp. 1-20.

Haughton Mifflin, "Estimate", The American Heritage dictionary of the English language (5th ed.), Jul. 24, 2017, 2 pages.

How BodyMedia FIT Works, <http://www.bodymedia.com/Shop/Learn-More/How-it-works>, accessed Jun. 17, 2011, 2 pages.

Internet Archive, Withings "Sleep Tracking Mat" Nov. 22, 2018. Retrieved from https://web.archive.org/web/20181122024547/https://www.withings.com/us/en/sleep (Year: 2018).

Jaines, Kira, "Music to Help You Fall Asleep," <http://www.livestrong.com/article/119802-music-fall-sleep/>, May 10, 2010, 2 pages.

JETLOG Reviewers Guide, <http://www.jetlog.com/fileadmin/Presse_us/24x7ReviewersGuide.pdf>, 2009, 5 pages.

Leeds, Joshua, "Sound-Remedies.com: Sonic Solutions for Health, Learning & Productivity," <http://www.sound-remedies.com/ammusforslee.html>, Accessed May 23, 2013, 2 pages.

Lichstein, et al., "Actigraphy Validation with Insomnia", Sleep, vol. 29, No. 2, 2006, pp. 232-239.

Liden, Craig B, et al, "Characterization and Implications of the Sensors Incorporated into the SenseWear(TM) Armband for Energy Expenditure and Activity Detection", , accessed Jun. 17, 2011, 7 pages.

Mattila et al., "A Concept for Personal Wellness Management Based on Activity Monitoring," Pervasive Computing Technologies for Healthcare, 2008.

Patel, et al., Validation of Basis Science Advanced Sleep Analysis, Estimation of Sleep Stages and Sleep Duration, Basis Science, San Francisco, CA, Jan. 2014, 6 pages.

Pires, P. D. C. Activity Characterization from Actimetry Sensor Data for Sleep Disorders Diagnosis, Universidade T ecnica de Lisboa, Sep. 2008, 10 pages.

Pollak et al., "How Accurately Does Wrist Actigraphy Identify the States of Sleep and Wakefulness?", Sleep, vol. 24, No. 8, 2001, pp. 957-965.

Power Nap, <en.wikipedia.org/wiki/Power.sub.-nap>, Last Modified Sep. 20, 2012, 4 pages.

PowerNap iPhone App, <http://forums.precentral.net/webos-apps-software/223091-my-second-app---powernap-out-app-catalog-nap-timer.html>, Jan. 6, 2010, 10 pages.

Rechtschaffen et al., Manual of Standardized Terminology, Techniques and Scoring System for Sleep Stages of Human Subjects, 1968, 57 pages.

Sara Mednick, <en.wikipedia.org/wiki/Sara.sub.-Mednick>, Last Modified Sep. 12, 2012, 2 pages.

Schulz et al. "Phase shift in the REM sleep rhythm." Pflugers Arch. 358, 1975, 10 pages.

Schulz et al. "The REM-NREM sleep cycle: Renewal Process or Periodically Driven Process?." Sleep, 1980, pp. 319-328.

Sleep Debt, <en.wikipedia.org/wiki/Sleep.sub.-debt>, Last Modified Aug. 25, 2012, 3 pages.

Sleep Inertia, <en.wikipedia.org/wiki/Sleep_inertia>, Last Modified Sep. 12, 2012, 2 pages.

Sleep, <en.wikipedia.org/wiki/Sleep.sub.-stages#Physiology>, Last Modified Oct. 5, 2012, 21 pages.

Slow Wave Sleep, <en.wikipedia.org/wiki/Slow-wave.sub.-sleep>, Last Modified Jul. 22, 2012, 4 pages.

Sunseri et al., "The SenseWear (TM) Armband as a Sleep Detection Device," available online at <http://sensewear.bodymedia.com/SenseWear-Sludies/SW-Whilepapers/The-SenseWear-armband-as-a-Sleep-Delection-Device>, 2005, 9 pages.

Wikipedia, "David.sub Dinges", available online at <en.wikipedia.org/wiki/David.sub_Dinges>, Sep. 12, 2012, 2 pages.

Yassourdidis et al. "Modelling and Exploring Human Sleep with Event History Analysis." Journal of Sleep Research, 1999, pp. 25-36.

\* cited by examiner

Single Sensor

Multi Sensor

Sensor Array

SLEEP SURFACE SENSOR BASED SLEEP ANALYSIS SYSTEM

RELATED APPLICATION

The present application claims priority to U.S. Provisional Application No. 62/133,734 filed on Mar. 16, 2015, and incorporates that application in its entirety.

FIELD

The present invention relates to sleep analysis, and more particularly to providing sleep analysis through a sleep surface.

BACKGROUND

An average person spends about one-third of his or her life asleep. Sleep is the time our bodies undergo repair and detoxification. Research has shown that poor sleep patterns is an indication of and often directly correlated to poor health. Proper, restful and effective sleep has a profound effect on our mental, emotional and physical well-being.

Every person has a unique circadian rhythm that, without manipulation, will cause the person to consistently go to sleep around a certain time and wake up around a certain time. For most people, a typical night's sleep is comprised of five different sleep cycles, each lasting about 90 minutes. The first four stages of each cycle are often regarded as quiet sleep or non-rapid eye movement (NREM). The final stage is often denoted by and referred to as rapid eye movement (REM). REM sleep is thought to help consolidate memory and emotion. REM sleep is also the time when blood flow rises sharply in several areas of the brain that are linked to processing memories and emotional experiences. During REM sleep, areas of the brain associated with complex reasoning and language experience blood flow declines, whereas areas of the brain associated with processing memories and emotional experiences exhibit increased blood flow.

BRIEF DESCRIPTION OF THE FIGURES

The present invention is illustrated by way of example, and not by way of limitation, in the figures of the accompanying drawings and in which like reference numerals refer to similar elements and in which:

FIG. 1A is network diagram of one embodiment of the system, including the elements communicated with.

DETAILED DESCRIPTION

An improved sleep surface based sleep analysis system is described. This system can also be referred to as an in-bed sensor system. The system includes one or more sensors arranged underneath sleeping surface, such as a mattress, mattress topper, or other portion of the sleeping surface. The sensor portion of the system is designed to be placed sufficiently remotely from the user that the shape of the sensor cannot be felt by a user. In one embodiment, the sensor is sufficiently sensitive to pick up micro-motions when placed underneath or in a mattress, on a box spring, on or in slats, on or in an adjustable base, on or in a platform or another configuration that provides a solid base underneath a mattress. In one embodiment, the sensor system can be retrofitted into an existing bed. In one embodiment, the LDC1000, LDC1612, or LDC1614 inductor sensor system from TEXAS INSTRUMENTS® is used as the inductive sensor. A different inductor sensor may be used. Alternatively or additionally, other types of sensors, such as accelerometers may be used, as long as they are sufficiently sensitive to pick up user micro-motions.

In one embodiment, the system may be incorporated into a box spring, foundation, base, mattress, or mattress topper. In one embodiment, the output of the sensor is coupled to the rest of the sensor system via a cable. In one embodiment, a cable provides power to the sensor, and is used to send data from the sensor to the other parts of the sensor system. In one embodiment, the sensor may be separately powered, and data may be transmitted using a network connection such as Bluetooth or Wi-Fi, or another format. In one embodiment, power and data may both be transmitted wirelessly. In one embodiment, the sensor is coupled to a processor, which is coupled to a mobile device and/or a network.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1A:
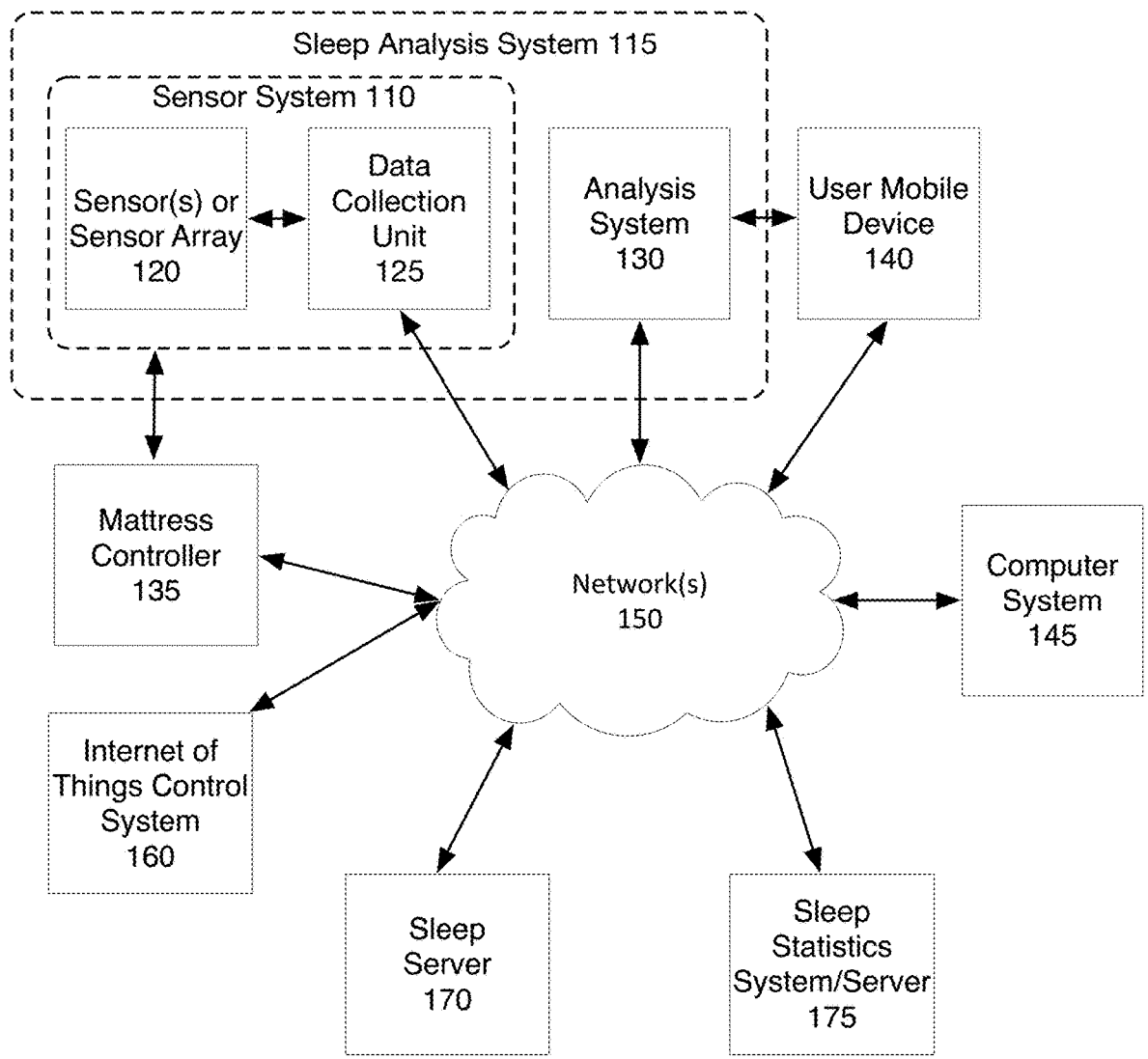

FIG. 1A is network diagram of one embodiment of the system, including the elements, and their communication. The system includes a sensor system 110, which includes a sensor or sensor array 110 and a data collection unit 125. The sensor system 110 is part of a sleep analysis system 115, which includes sensor system and analysis system 130. In one embodiment, the data collection unit 125 and analysis system 130 may be implemented in the same device. Alternately, the analysis system 130 may be remote and separate from the sensor system 110. In one embodiment, the data collection unit 125 is located within the foundation/mattress/bed, and the analysis system 130 is implemented externally. In one embodiment, the analysis system 130 includes a processor which receives power from a plug-in power supply. In one embodiment, the analysis system 130 has a form factor comparable to a power brick.

In one embodiment, the analysis system 130 communicates with a user mobile device 140. The connection between analysis system 130 and user mobile device 140 may be via a network 150, such as via a WiFi connection or cellular network connection. The connection may be via a local area network or personal area network, such as Bluetooth. In one embodiment, the connection may be physical wireline connection. The user mobile device 140 may be a smart phone, a tablet, or another device, which provides additional user interface features and controls. In one embodiment, the connection may be provided through a docking station, or similar connection element, which physically connects to sleep analysis system 115 and the user mobile device 140.

In one embodiment, the sleep analysis system 115 may additionally or alternatively connected to a computer system 145 or a server 170, via network 150, such as Bluetooth, WiFi, or another type of connection. In one embodiment, the user mobile device 140 and/or the sleep analysis system 130 may provide controls to devices which are part of the Internet of Things 160. The Internet of Things 160 may include elements of a smart home, or environment, and provide controllers for a smart bed, lights, thermostats, coffee makers, window treatments, speakers, alarm clocks, and other aspects of the user's environment that may be controlled via commands through a network. The IoT system 160 may control IoT enabled elements to assist in optimizing the user's sleep and health.

In one embodiment, some or all of the user data may further be transmitted to a sleep server 170, which can provide additional analysis, in one embodiment. In one embodiment, user data is stored on the mobile device. In one embodiment, collective anonymized user data is stored by sleep statistics system/server 175. The sleep statistics system/server 175 utilizes the abstracted data to analyze sleep patterns across large populations, correlated by user characteristics. The system 175 in one embodiment, includes data from millions of nights of sleep, and uses that data to provide recommendations to users and adjustments to the system.

Figure 1B:
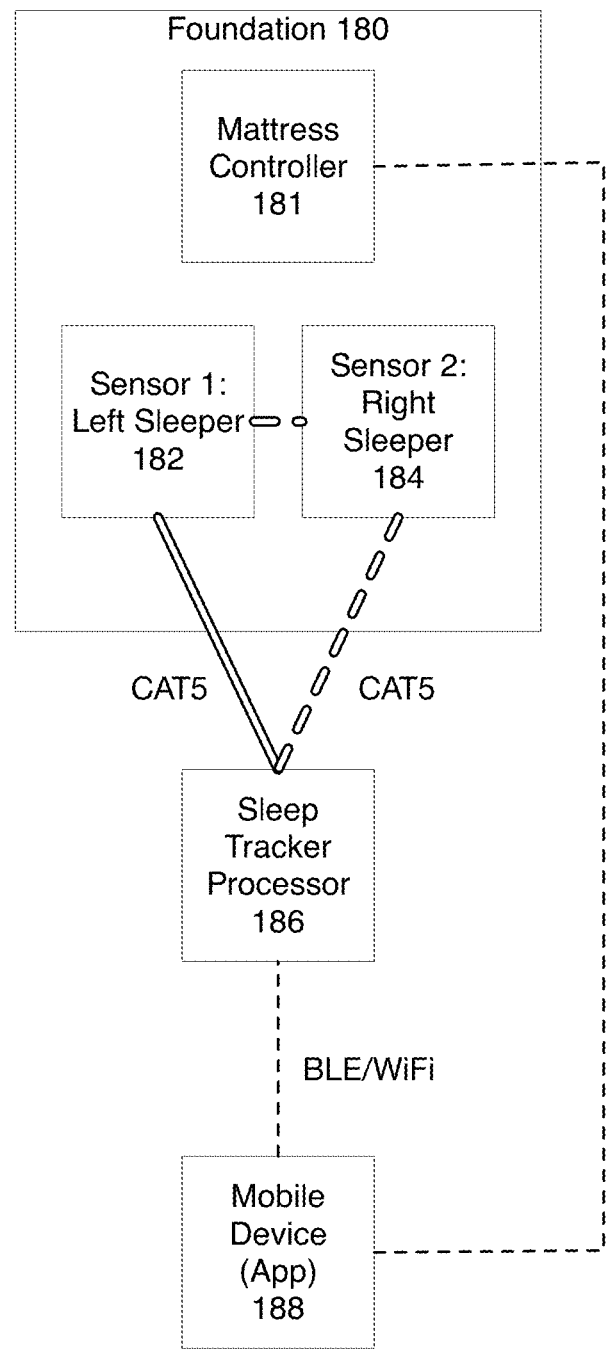
FIG. 1B is a diagram showing the configuration of the system, according to one embodiment

FIG. 1B is a diagram showing the configuration of the system, according to one embodiment The bed or foundation 180 includes two sensors, in one embodiment, sensor 1 for the left sleeper 182, and sensor 2 for the right sleeper 184. The sensors 182, 184 are coupled to a sleep tracker processor 186. In one embodiment, each sensor 182, 184 has a cable coupling it to the sleep tracker processor 186. In another embodiment, one sensor 184 is coupled to the other sensor 182, which in turn is coupled to the sleep tracker processor 186, meaning that only one cable extends from the bed. In one embodiment, the connection between the sensor(s) 182/184 and the sleep tracker processor 186 is a CAT5 cable, using an RJ45 plug in the sleep tracker processor 186 and sensor(s) 182, 184. The connection, in one embodiment, provides power to the sensors 182, 184, and sends data from the sensors 182, 184 to the sleep tracker processor 186.

The sleep tracker processor 186 in one embodiment connects to an application on a mobile device 188 via a wireless connection. In one embodiment, the wireless connection is a low-power Bluetooth (BLE) connection. The connection may be continuous, periodic, or intermittent. In another embodiment, the connection is a Wi-Fi connection, or another type of wireless connection. In one embodiment, the mobile device 188 may be connected to the sleep tracker processor 186 via a wired connection.

Figure 2A:
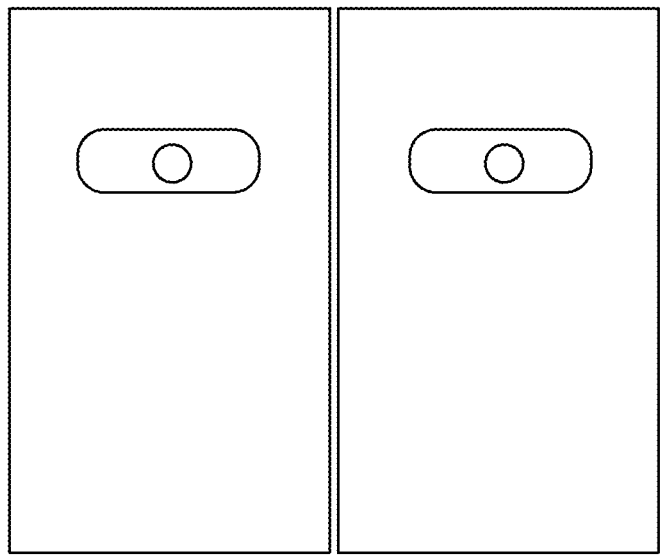
FIGS. 2A-2I are diagrams showing various exemplary configurations of the sensors or sensor arrays in the system.
Figure 2B:
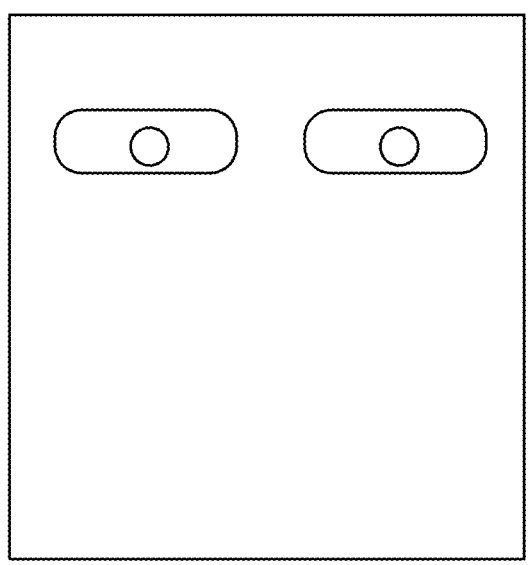
Figure 2C:
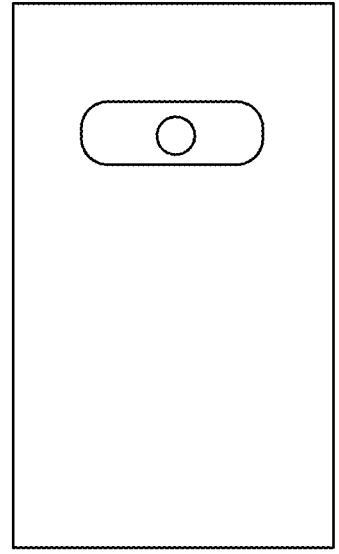

FIGS. 2A-2I are diagrams showing various exemplary configurations of the sensors or sensor arrays in the system. In one embodiment, there may be a single sensor per person, located at approximately the chest level, as shown in FIGS. 2A-C. This enables the sensor to pick up breathing and the heart rate as well as micro-movements, in one embodiment.

Figure 2D:
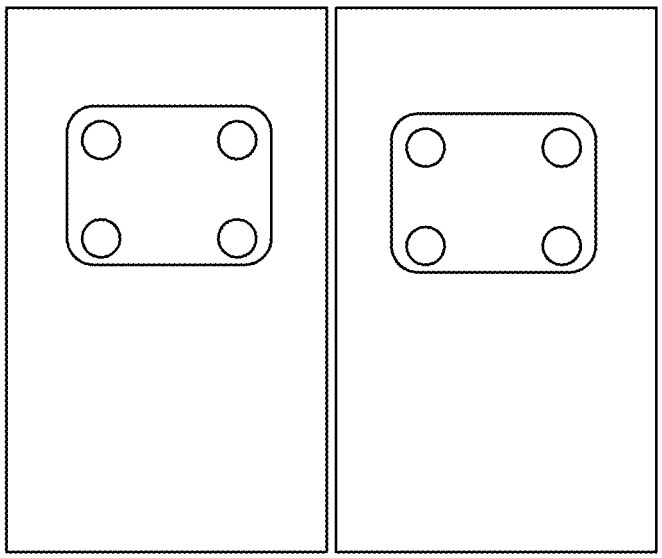
Figure 2E:
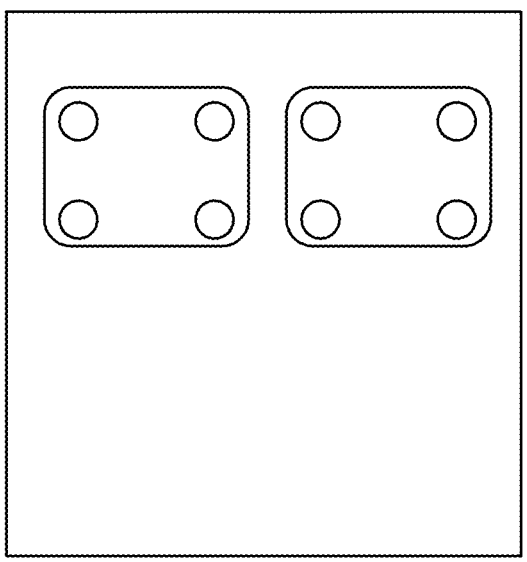
Figure 2F:
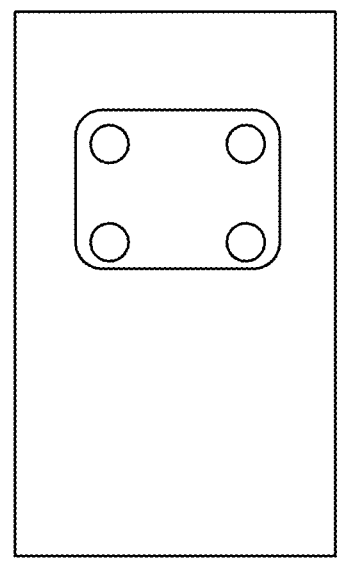

Alternatively, a sensor array may include multiple sensors, as shown in FIGS. 2D-2F, in which a set of four sensors are placed per each expected sleeper. In one embodiment, the sensors are distributed at approximately head to mid-chest height, to optimally track the user's heart rate, breathing, and micro-movements.

In one embodiment, these sensors may each be separate sensors with connections to the other sensors or the sleep tracker processor. In one embodiment, the sensors may be spaced in a rectangle, at head and mid-chest height of a user. Alternative configurations of a multi-sensor array may be used.

Figure 2G:
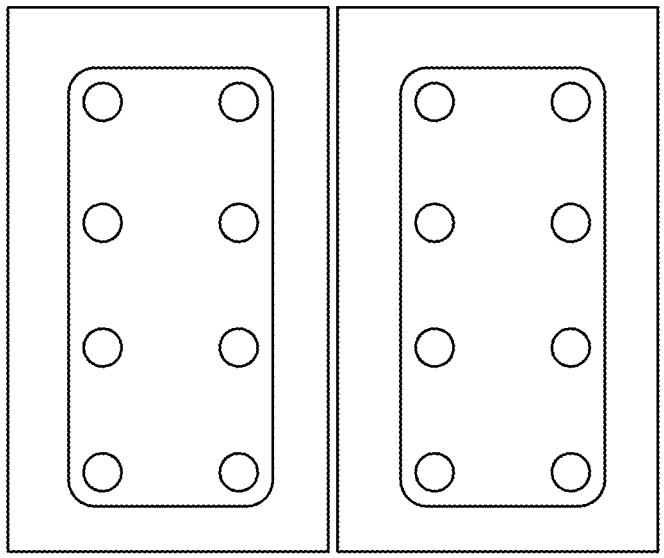
Figure 2H:
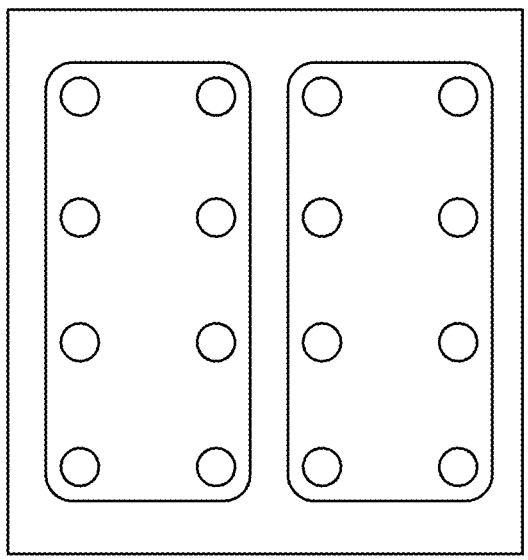
Figure 2I:
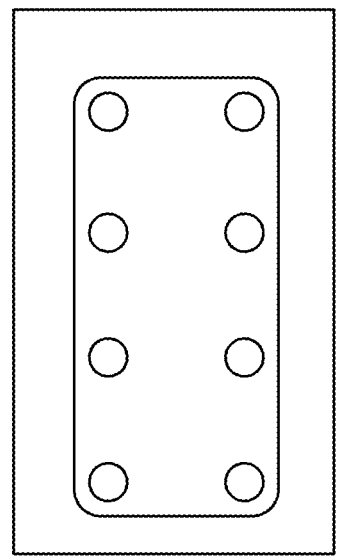

FIGS. 2G-2I show sensors arrays which include sensors all along the body, form head to toe, in one embodiment. In one embodiment, eight sensors are evenly distributed through the sensor array. Alternative configurations may be used. The sensor array may cover the bed, to provide the most complete data. In one embodiment, the number of sensors in a bed may vary from a single sensor to as many as sixteen sensors or more. The manufacturer or buyer may balance the cost of the additional sensors with the additional data available as a result of having those sensors.

The sensors in one embodiment, are connected in parallel, or series, to a data collection mechanism, which provides power to the sensors and provides the sensor data to the sleep tracker processor. In one embodiment, the sensor itself may have a small buffer for collected data, so that the sensor data may be passed through a s ingle cable, using sequential or parallel encoding.

Figure 2J:
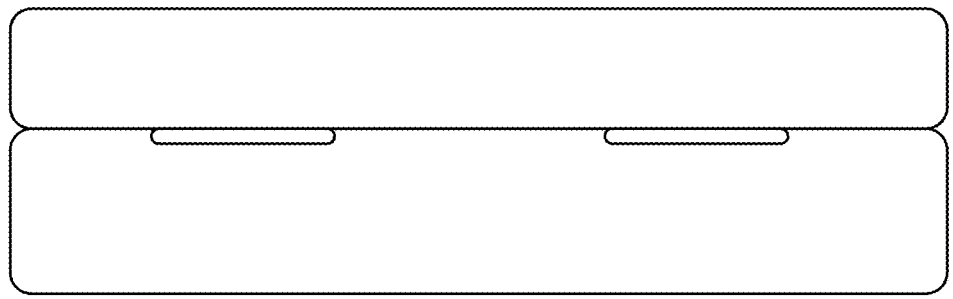
FIGS. 2J-2M are cross-sections of a bed including various exemplary configurations of sensors.

The sensors may be located in various locations within the bed structure, as shown in FIG. 2J-2M. In one embodiment, the sensors may be located within the foundation, as shown in FIG. 2J. In such a configuration, the sensor may be in a compartment within the foundation, with an exposed top that translates movement of the mattress to sensor data.

Figure 2K:
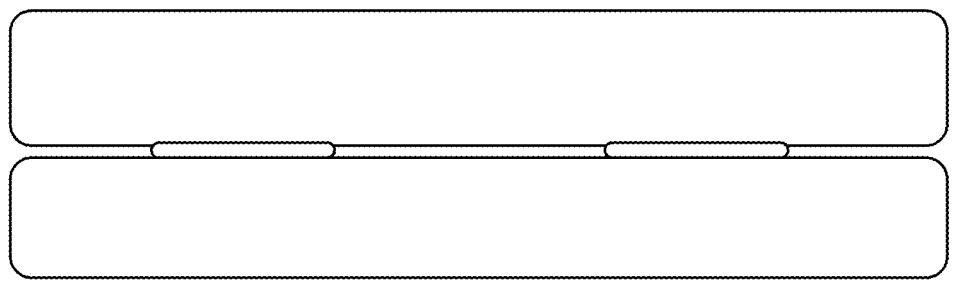

In one embodiment, the sensor may be located between the foundation and the mattress, as shown in FIG. 2K, enabling the system to be retrofitted onto an existing bed, without requiring a new foundation.

Figure 2L:
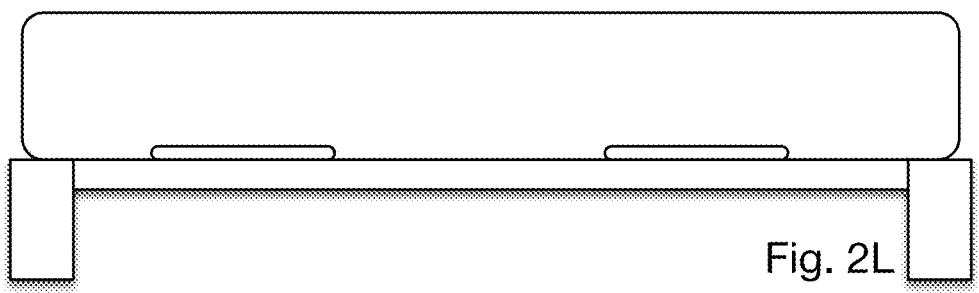
Figure 2M:
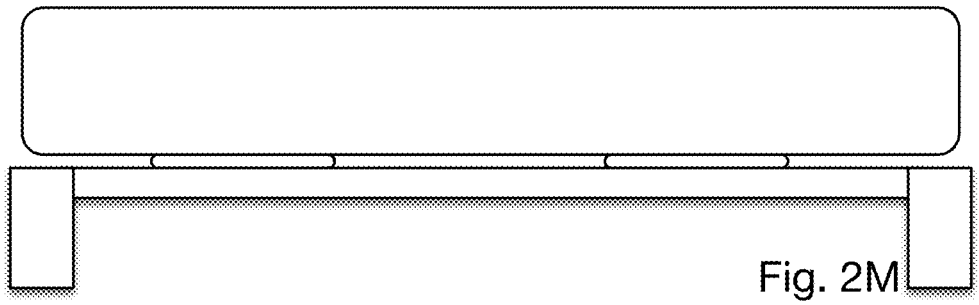

In one embodiment, in a configuration without a foundation or box spring, as shown in FIG. 2L, the system may be installed within the mattress, on the bottom of the mattress. Alternative, it may be within the bed frame, or placed on the frame underneath the mattress. Other configurations may also be used. In one embodiment, the user may purchase slats or a base board for a bed, including the sensor, to retrofit an existing bed frame to include the in-bed sleep sensor.

Figure 2N:
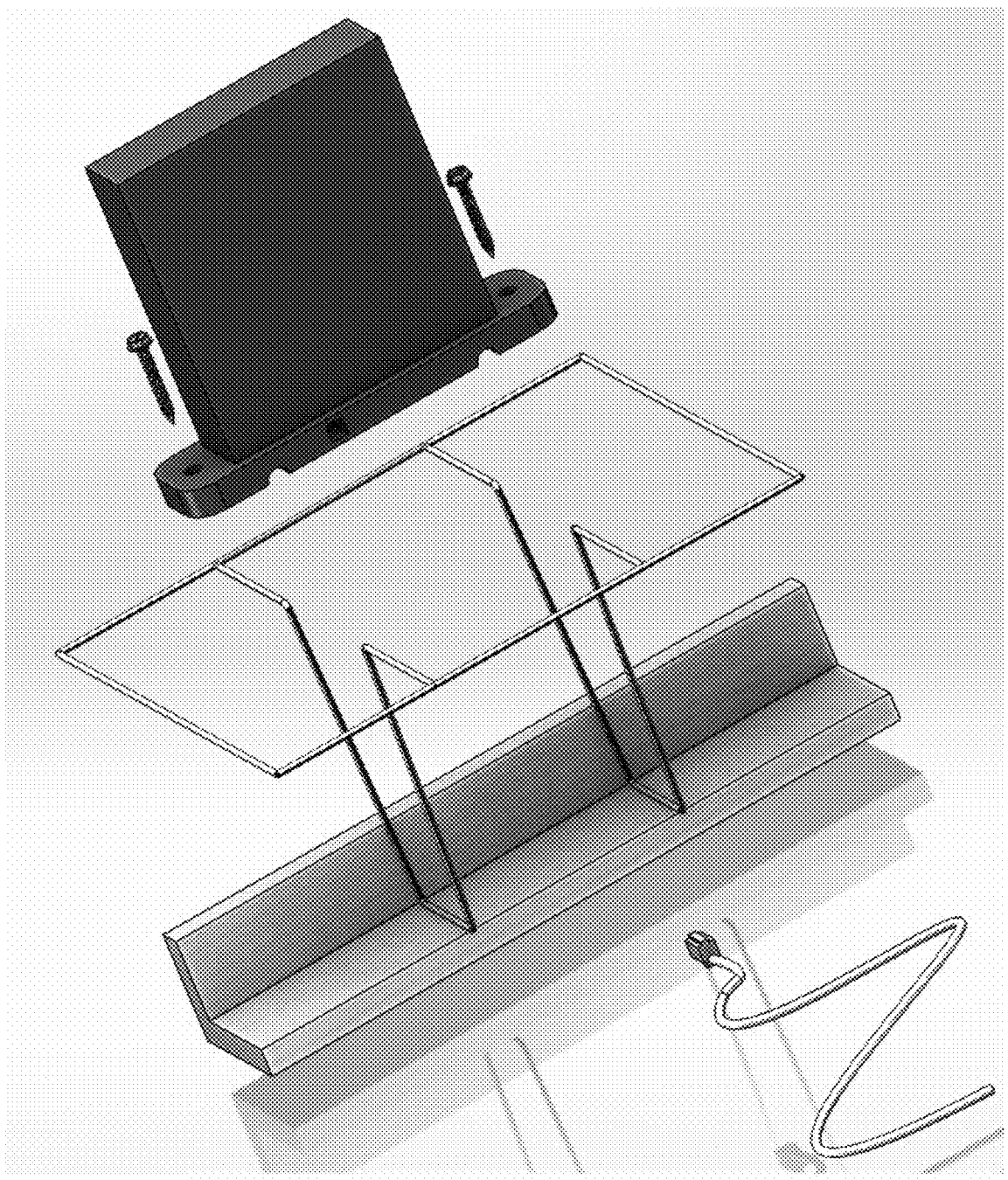
FIGS. 2N-2Q show images of one embodiment of the sensor and how it is placed within a foundation.
Figure 2O:
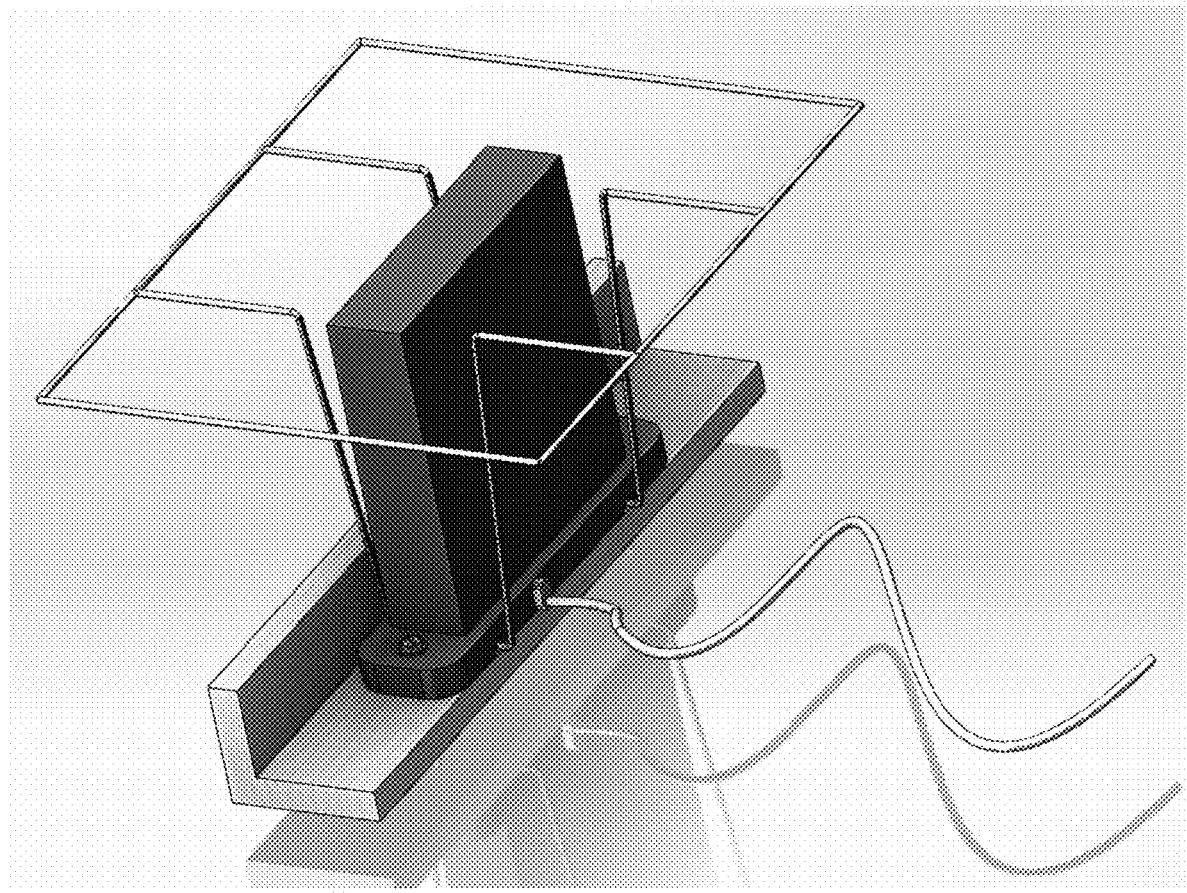

FIGS. 2N-2Q show images of one embodiment of the sensor and how it is placed within a foundation, mattress, or bed frame. FIG. 2N shows in one embodiment of the sensor being placed into the foundation or box spring. In one embodiment, the system can be placed with two screws which are screwed into the wooden frame of the box spring. FIG. 2O shows the exemplary configuration of one embodiment of the sensor system installed in a foundation. The metal framing above the sensor is part of the box spring configuration.

Figure 2P:
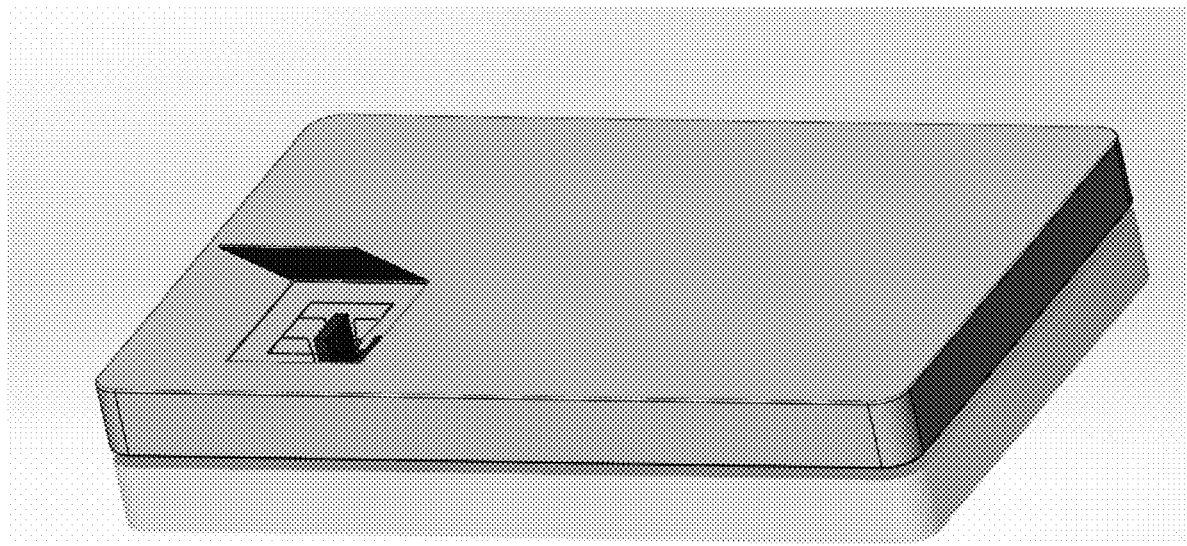
Figure 2Q:
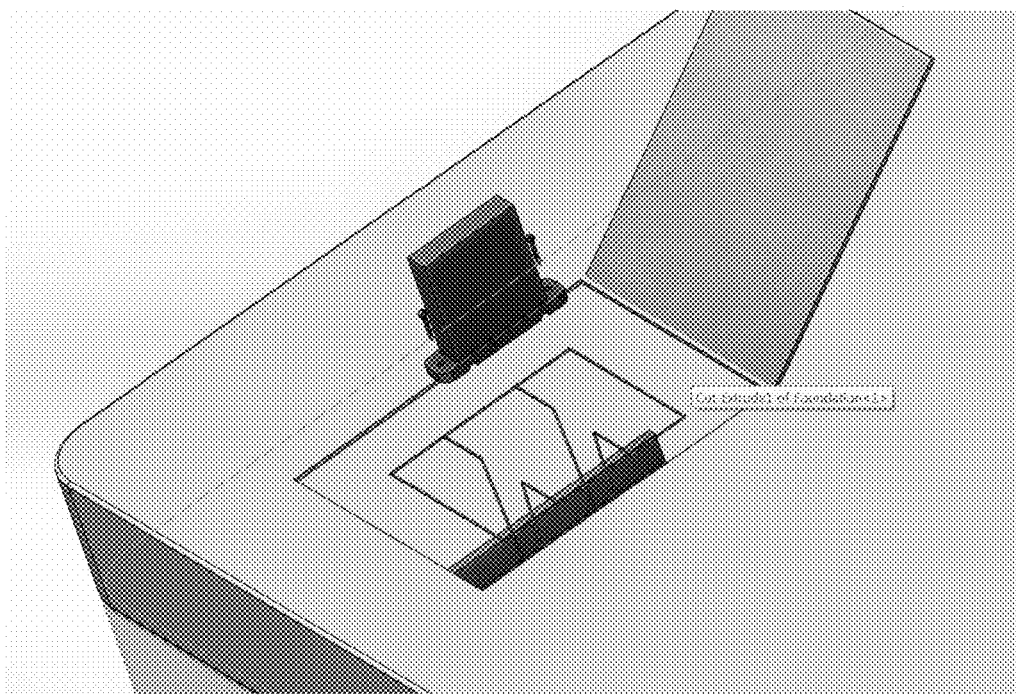

FIG. 2P-2Q shows one embodiment, of how the sensors system can be retrofitted into an existing foundation, by installing a flap where the sensor system may be inserted. In one embodiment, the flap may not be necessary when the sensor system is installed during the manufacturing cycle, prior to adding the cover to the box spring. Because the sensor system is powered externally through a cable, it need not be touched by a consumer.

Figure 2R:
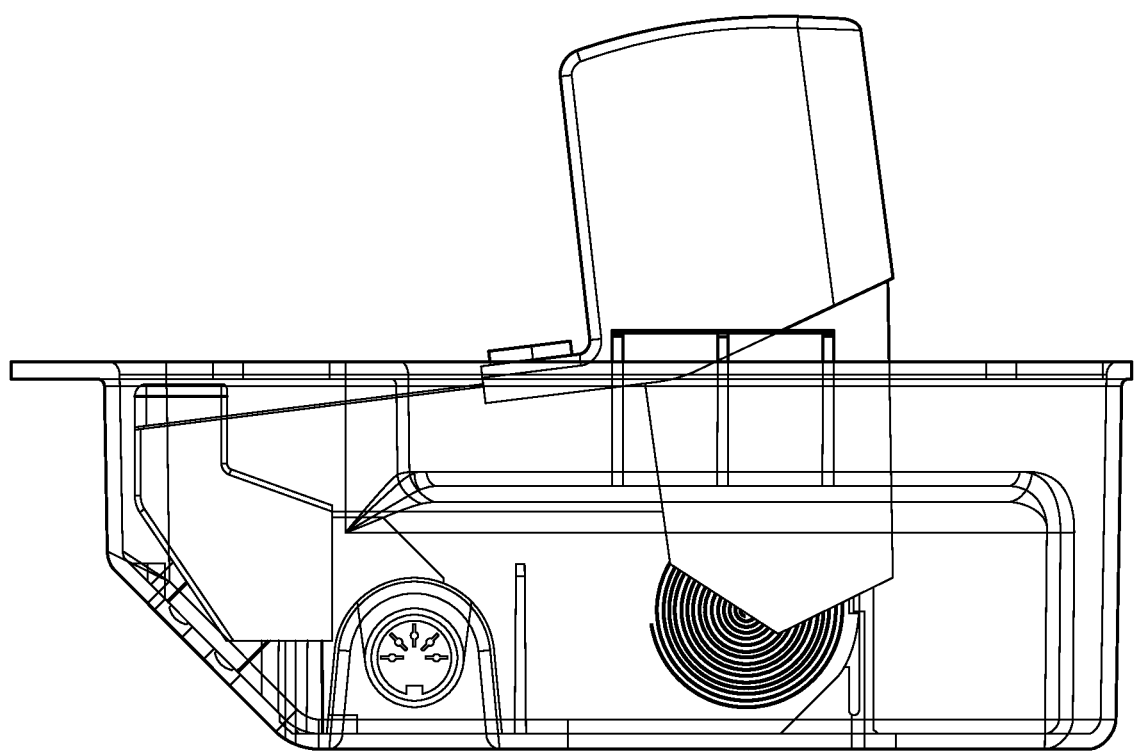
FIGS. 2R-2S show another embodiment of the sensor, which may be placed within a foundation or mattress.
Figure 2S:
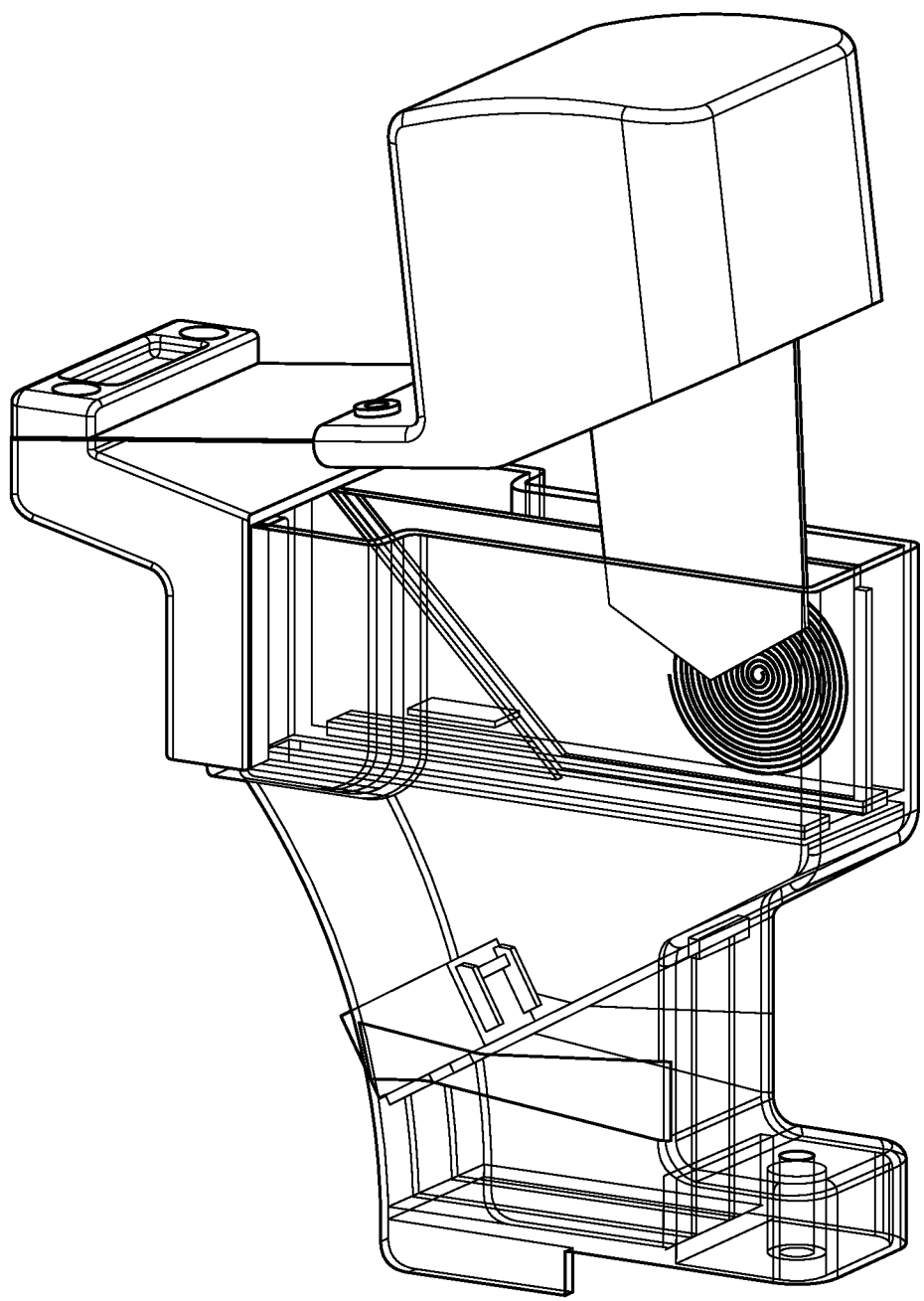

FIG. 2R-2S shows an alternative configuration in which the coils of the sensor are fixed, and the metallic portion is located on a hinged element, which moves with the movements of the mattress. This configuration may be embedded in a bedframe, foundation, or box spring. FIG. 2S shows a translucent version, showing the positioning of the plug at the bottom, the hinged elements a the top, and the sensor coils.

Figure 3A:
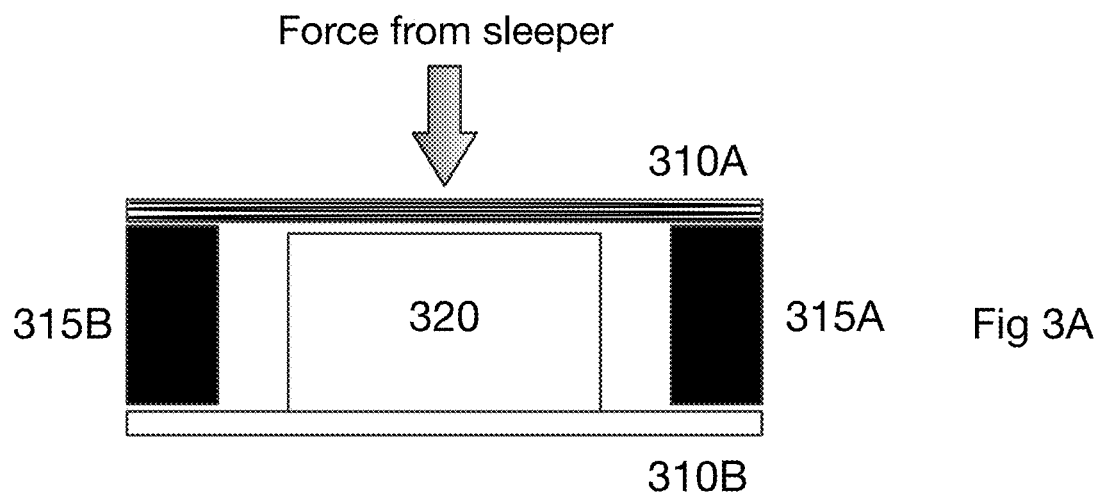
FIGS. 3A-3C are diagrams showing configurations of the sensor and sensor case, which may be used with the present invention.
Figure 3B:
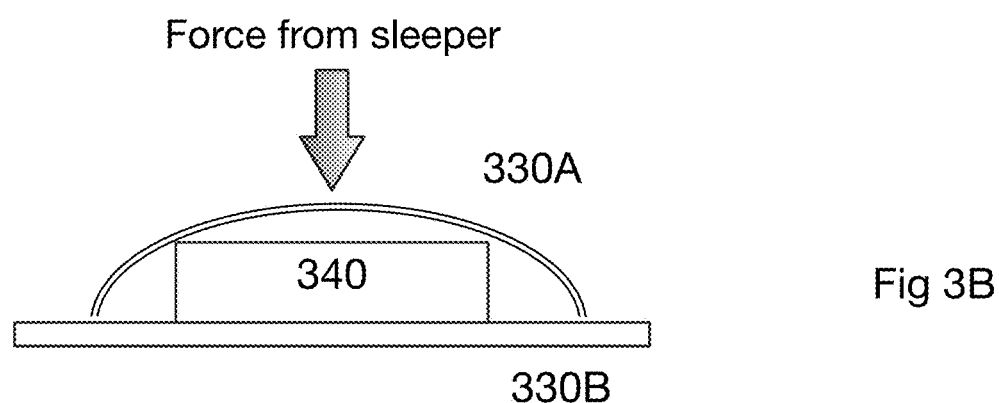
Figure 3C:
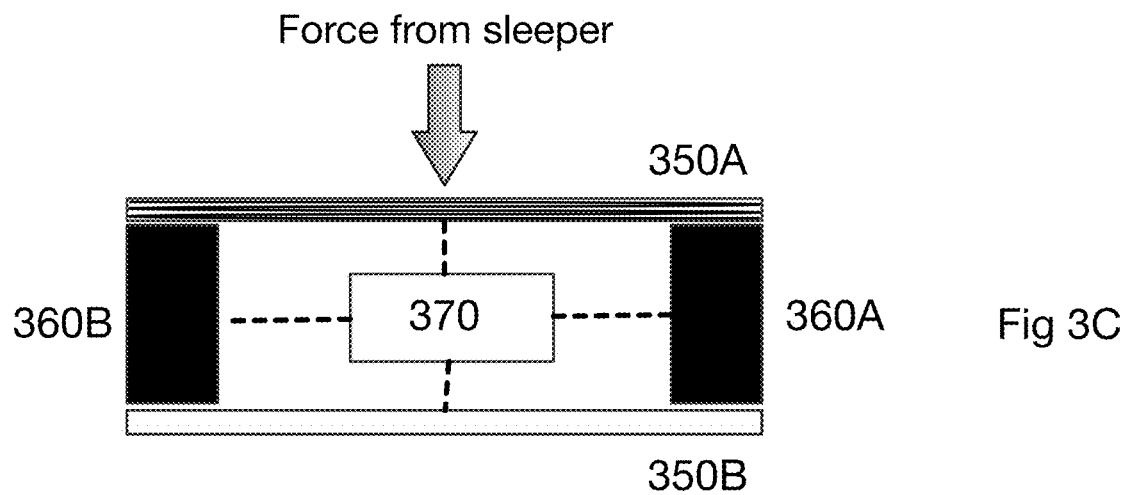

FIGS. 3A-3C are diagrams showing configurations of the sensor and sensor case, which may be used with the present invention. These configurations are alternate embodiments from the configuration described above with respect to FIGS. 2R-2S.

In one embodiment, shown in FIG. 3A, the sensor 320 is within sensor case, having a top 310A and bottom 310B. In one embodiment, compressible sides 315A, 315B. The force from the sleeper's movements move the top 310A, which is sensed by sensor 320. In one embodiment, the sides 315A, 315B are made of a flexible material which does not compress completely when the user is laying on the bed, providing movement due to the micro-movements of the user, the user's heart beat, and other motions.

An alternative configuration, shown in FIG. 3B uses a curved top 330A which again provides some movement due to the user's motions and heart beat and breathing. In one embodiment, the curved cover 330A is made of metal, and calibrated so that it does not excessively compress even under a heavy sleeper.

Another configuration, shown in FIG. 3C, suspends the sensor 370 within the sensor case. This ensures that there is still motion possible even if the sides 360A, 360B are compressed significantly. In one embodiment, the sides 360A, 360B are made of foam. In one embodiment, the dimensions shown are merely to enable differentiation between the elements. The actual dimensions of the sensor 320, 350, 370 in one embodiment is 5.00 mm×4.00 mm.

Figure 3D:
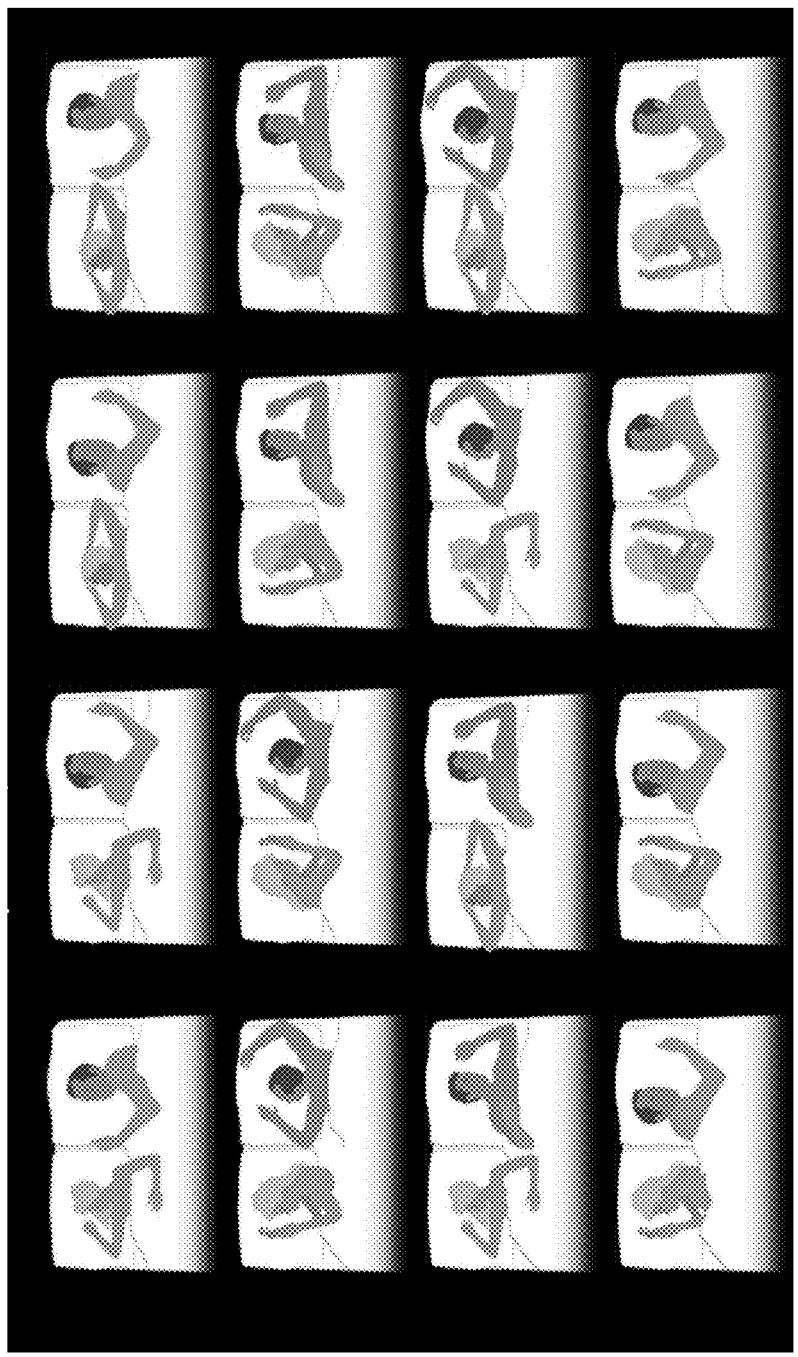
FIG. 3D is a diagram of one embodiment of various sleep configurations, which may be recognized by the system.

FIG. 3D is a diagram of one embodiment of various sleep configurations, which may be recognized by the system. The system in one embodiment is designed to identify the user's sleep configuration. Sleep configurations, in one embodiment include sleeping on the right side, left side, stomach, and back. In one embodiment, the system can differentiate the sleep configurations of both users, identifying the sixteen possible configurations illustrated in FIG. 3D. In one embodiment, additional configuration information may also be identified, for example the system may identify more details about the user's sleep configuration, such as how tightly the user is curled, the relative locations of the user's legs etc. The more data is available about the user's sleep, the more data can be used in correlating sleep state data and sleep quality.

Figure 4:
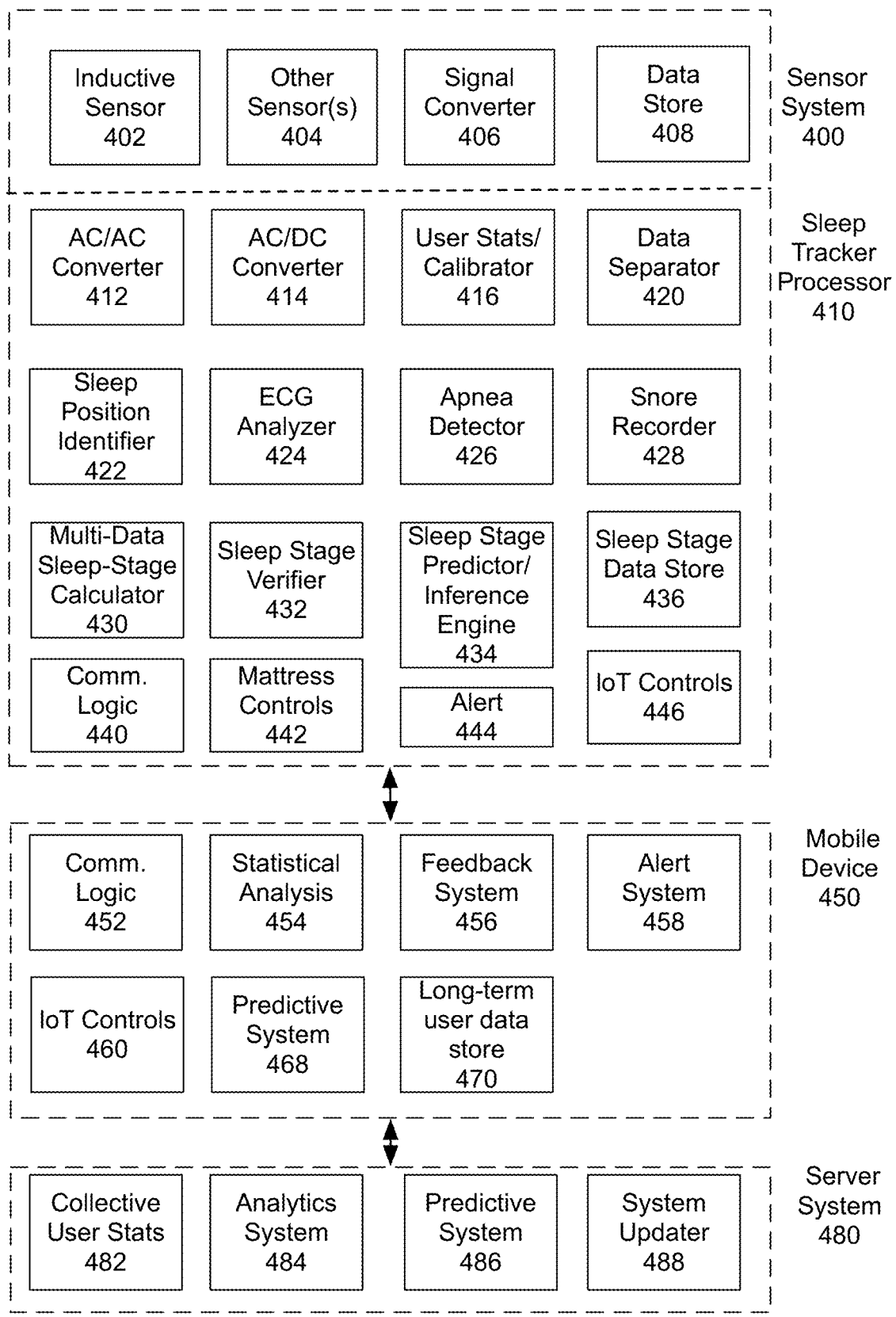
FIG. 4 is a block diagram of one embodiment of the sensor system and computer system.

FIG. 4 is a block diagram of one embodiment of the sleep detection system sensor system and computer system.

Sleep tracker processor 410 includes an AC/AC converter 412, to step down the AC voltage from the plug to a level that the sensor system 400 needs. In one embodiment, an AC/DC converter 414 provides power for the processor and other elements of the system, including the processor, and potentially other sensors 404.

The sensor system 400 includes inductive sensor 402 which may be built into the bed, as described above, and may receive low power AC power from AC/AC converter 412. The output of the inductive sensor 402, and other sensors 404 may be converted by signal converter 406 to a digital signal, prior to being sent to the sleep tracker processor via a cable. In one embodiment, sensor system 400 includes a local data store 408 to store sensor data. In one embodiment, the data store 408 may be used to buffer data.

In one embodiment, the in-bed portion of the system is the sensor system 400 including the inductive sensor 402, any other built-in sensors 404, and signal converter 406, powered through a cable from the sleep tracker processor 410. The converted signal is sent to the sleep tracker processor 410, which in one embodiment is an element plugged into the wall. In another embodiment, the raw sensor data may be sent to sleep tracker processor 410.

Sleep tracker processor 410 controls calibrator 416 which may be used to calibrate the inductive sensor 402. The calibration may be based on the user's characteristics, such as gender, weight, etc.

The data separator 420 separates the data from a plurality of sensors, if there are multiple sleepers. The data separator 420 in one embodiment further separates the breathing, micro-motion, and heart rate data. The data is then used by sleep position identifier 422 to identify the sleep position of each of the users in the bed.

ECG analyzer 424 analyzes the separated heart data. This data may be generally used to help identify sleep state. However, it can also be used to detect potential problems, such as arrhythmia.

Apnea detector 426 utilizes the breathing data to ensure that the user is breathing smoothly. Snore recorder 428 in one embodiment utilizes a microphone to record snoring. In one embodiment, the recorder 428 may include a detection mechanism and a trigger to turn on the microphone and recording when appropriate based on breathing data.

Multi-data sleep-state calculator 430 utilizes the heart rate, breathing, and micro-motion data, as well as any other data available, to identify the users' sleep states. In one embodiment, sleep-stage calculator 430 data is compared to the output of sleep stage predictor/inference engine 434 by sleep stage verifier 432. The real data is used to validate the prediction, rather than generate the sleep state directly from the data. In one embodiment, the inference engine 434 may utilize primarily the user's own data. However, in one embodiment, data collected over many users may be used to initially populate inference engine's data set. Sleep stage data store 436 stores the current & past sleep state data. This may be used by the inference engine 434, as well as communicated to server system 480, or mobile device 450.

In one embodiment, connection between sleep tracker processor 410 and mobile device 450 through communication logic 440/452 is intermittent, and the sleep tracker processor does not rely on the mobile device 450 for calculations or processing. In another embodiment, one or more of the logic blocks described may either be on the mobile device 450, or may be shared with the mobile device 450 such that the combination of the sleep tracker processor 410 and the mobile device 450 make the described calculations.

In one embodiment sleep tracker processor 410 further includes mattress controls 442 to control the mattress based on sleep stage and any other detected issues. Additionally, sleep tracker processor 410 may in one embodiment include alert system 444. In another embodiment, these logics may be part of mobile device 450.

Mobile device 450 receives data from sleep tracker processor 410, via its own communication logic 452. In one embodiment, the data is used by the mobile device 450 to perform statistical analysis on the data 454. Predictive system 468, in one embodiment, predicts future health issues. In one embodiment, the predictive system utilizes historical data and data from collective user statistics 482 provided by server system 480 to make smart predictions. In one embodiment, mobile device includes Internet of Things (IoT) control 460. Alternately or additionally such controls may be within sleep tracker processor 410. This enables adjustment of the user's environment to optimize sleep and minimize health risks.

Feedback system 456 utilizes the graphic display capabilities of the mobile device 450 to provide detailed feedback to the user about their sleep, and other data, in one embodiment.

In one embodiment, sleep tracker processor 410 connects to server system 480 either directly or through mobile device 450. Server system 480 collects anonymized user statistics 482 and provides a high power big data analytics system 484, to make predictions, which may be provided to the user's system, and shown to the user. The predictions may be provided to the user as recommendations. For example, if the system determines that when users sleep less than 6 hours a day for more than 3 days in a row, they are much more likely to get ill, it may warn the user prior to that threshold being met that he or she needs to sleep more.

In one embodiment, server system 480 also includes system updater 488 which may push updates to inductive sensor and sleep tracker processor 410. This remote update capability means not only that the calibration and prediction is accurate, but also that if a problem is discovered it can be remedied without requiring access to the mattress by IT personnel.

Figure 5:
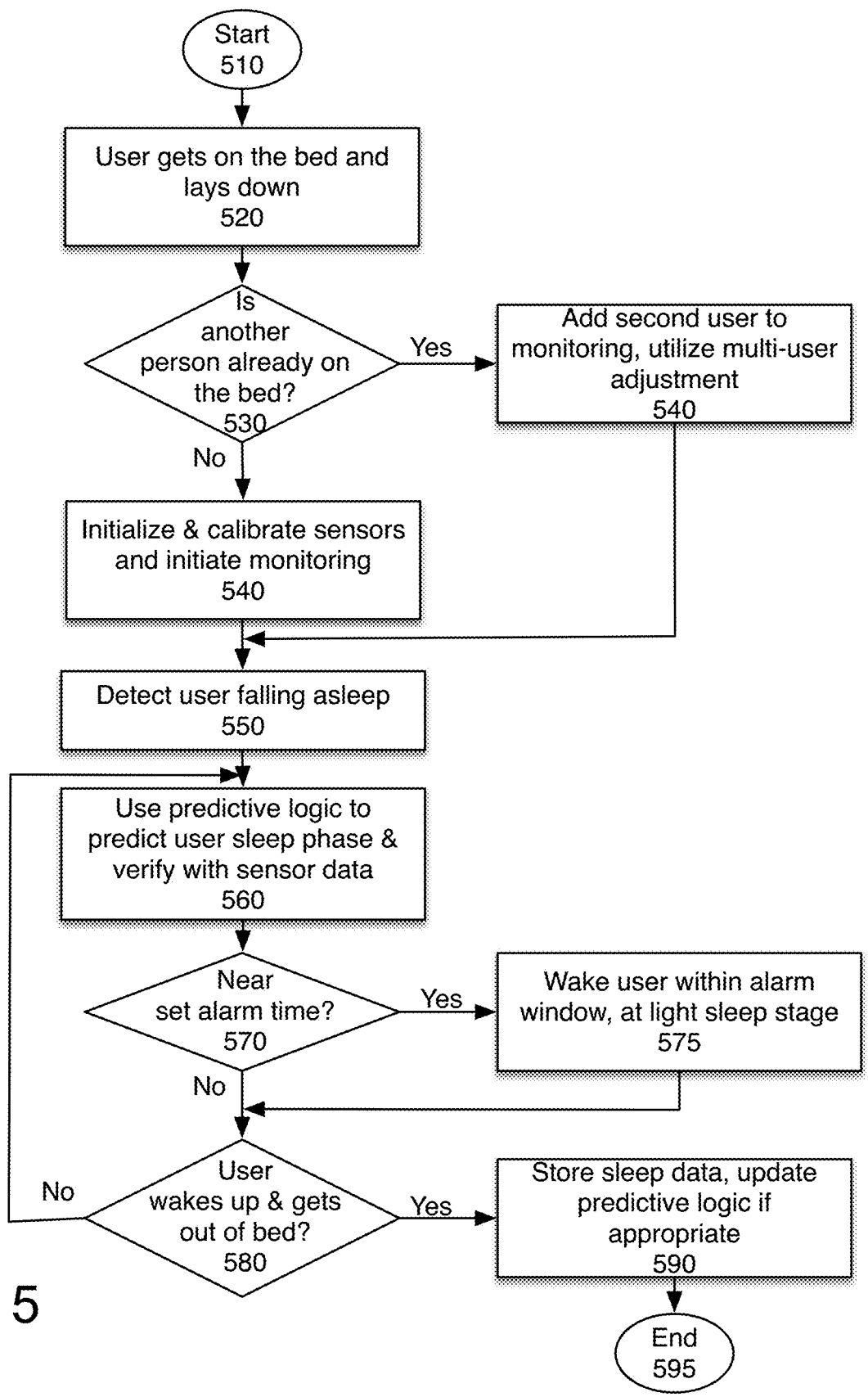
FIG. 5 is a flowchart of one embodiment of using the system.

FIG. 5 is a flowchart of one embodiment of using the system. The process starts at block 510. In one embodiment, this process is initiated when the system is turned on.

At block 520, the user gets on the bed, and lays down. In one embodiment, the system detects the user getting on the bed, as well as identifying when the user lays down.

At block 530, the process determines whether there is another person on the bed already. If so, the second user is added to the monitoring, and multi-user adjustment is utilized, at block 540. Multi-user adjustment monitors the relative data between the users to accurately attribute data to the correct user. Because the sensor is very sensitive, a sensor on the right side of the bed is capable of picking up movement from the user laying on the left side of the bed.

If there is no other user on the bed, at block 540 the sensors are initialized and monitoring is initiated. In one embodiment, initializing the sensor includes calibration. In one embodiment, the sensor is calibrated each time a person gets onto the bed. In one embodiment, if the bedframe is adjustable, when the bedframe is adjusted the sensor is recalibrated. In one embodiment, the system can be utilized for a fully adjustable bed, such as the Simmons NuFlex Adjustable Bed Base™, which can be positioned at many angles with a moveable head and foot portion. Because the sensor system is built into the base, in one embodiment, and calibrates when the bed is reconfigured, it can be used regardless of the positioning of an adjustable bed.

At block 550, the process detects the user falling asleep. When the user falls asleep the movements, and heart rate change, and this is used to detect the user falling asleep.

At block 560, the system uses predictive logic to predict the user's sleep phase, and verifying the predicted state using sensor data. The use of the predictive logic reduces the processing time and complexity for correctly identifying the user's sleep state and status.

At block 570, the process determines whether it's near the alarm time. If it is near the alarm time, at block 575, the user is woken within the alarm window, at a light sleep stage, as detected by the system. The process continues to block 580. If it's not near the alarm time, the process continues directly to block 580.

At block 580, the process determines whether the user woke up and got out of bed. If so, at block 590, the sleep data is stored. In one embodiment, the predictive logic is updated, if needed. In one embodiment, the predictive logic is customized based on data about the user. Therefore, as additional data is acquired, the predictive logic is continuously updated to ensure that the system correctly predicts and responds to the user's sleep states. In one embodiment, the system can also monitor the user's health, and can respond to that data appropriately as well. The process then ends at block 595.

If the user has not woken up and gotten out of bed, at block 580, the process continues to use predictive logic and monitor the user's state. In one embodiment, this may continue even after an alarm. In one embodiment, if the user does not get out of bed with an alarm, the system may adjust the alarm settings to increase the likelihood that the user will wake up and get out of bed.

Figure 6:
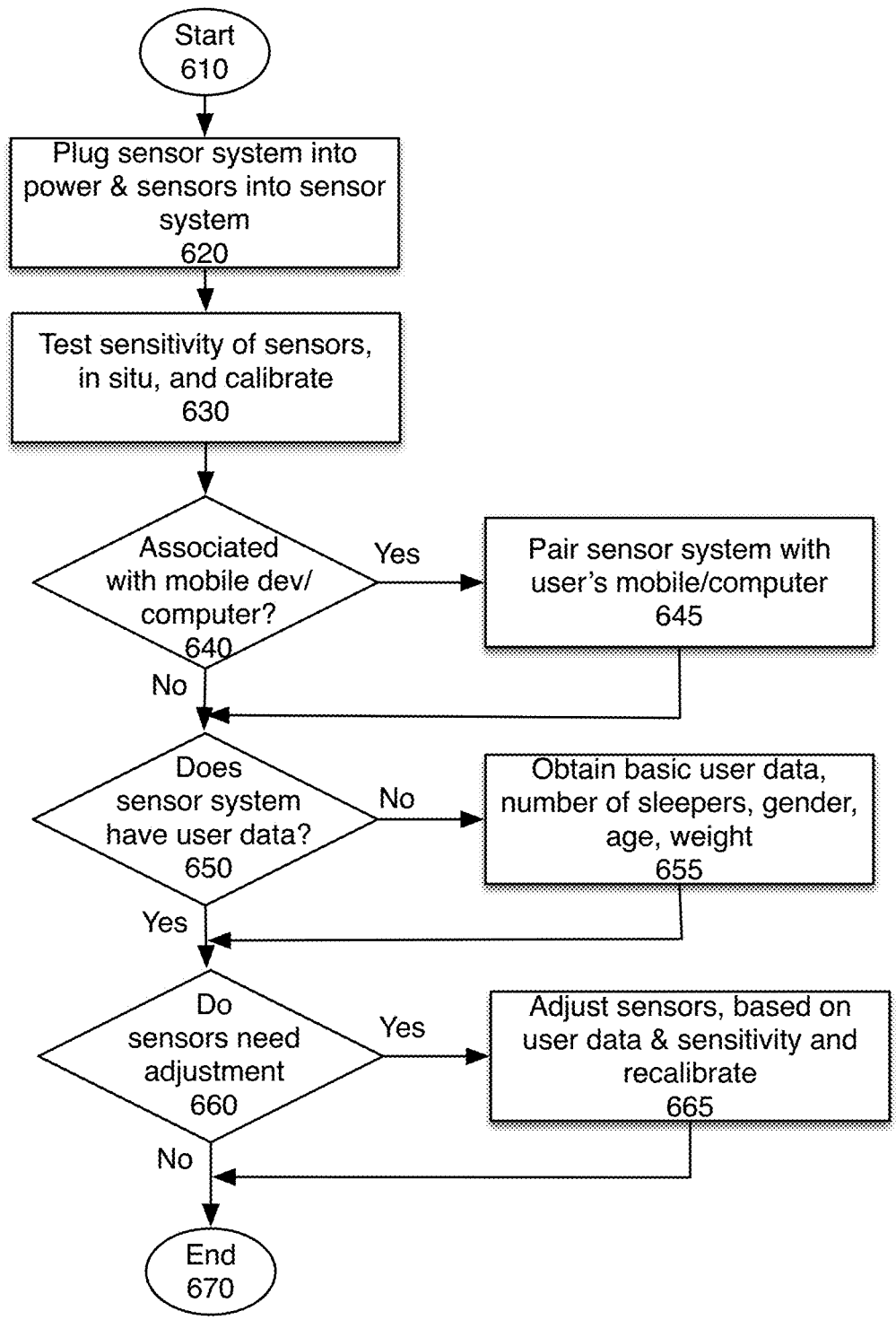
FIG. 6 is a flowchart of one embodiment of configuring the system.

FIG. 6 is a flowchart of one embodiment of configuring the system. The process starts at block 610. In one embodiment, this process takes place when the system initially is set up.

At block 620, the data collection unit is plugged into power, and the sensors are plugged into the data collection unit. In one embodiment, the sensors are connected to the data collection unit via a CAT5 cable. In another embodiment, a separate power cable and data cable is used.

At block 630, the sensitivity of the sensors is tested in situ. In one embodiment, once the sensor is in place (e.g. in its final location) its sensitivity is tested, and it is calibrated. Calibration ensures that the sensor is functional. In one embodiment, if there is a problem, the system a message may be sent to get any issues corrected. In one embodiment, calibration is a self-calibration.

At block 640, the process determines whether the system has been associated with a mobile device, application, or computer. In one embodiment, the system is designed to be paired with a device that provides additional user interface features. If the system has not yet associated, the process at block 645 pairs the sensor system with the user's mobile device, computer, or application. The process then continues to block 650. In one embodiment, the system uses a Bluetooth local area network, and utilizes standard Bluetooth discover methods.

At block 650, the process determines whether the sensor system has user data. User data, in one embodiment, includes user characteristic data. In one embodiment, characteristic data may include one or more of the user's gender, age, height, health, and athletic ability. In one embodiment, this data may be available from the paired device. For example, if the user has an existing health application on the user's mobile device, this data may be available. The user may also have added this data to the application already.

At block 655, the basic user data is obtained. In one embodiment, basic user data may include user characteristics as well as usage characteristics. Usage characteristics indicate the number of sleepers on the bed, and in one embodiment the sleep configuration. Sleep configuration indicates where each user sleeps, and which position they sleep in. In one embodiment, the system requests this data from the user. The process then continues to block 660.

At block 660, the process determines whether the sensors need adjustment. In one embodiment, this determination is made based on the user data and sensor calibration and sensitivity data. If the sensors do not need adjustment, the process ends at block 670. If the sensor needs adjustment at block 665, the sensor is adjusted. In one embodiment, the sensor adjustment may be based on user weight and sleep position, as well as sleep configuration data. In one embodiment, the adjustment reduces sensitivity for a larger user, and increases sensitivity for a smaller user. Other types of adjustments available in the sensor system may be used. After a sensor adjustment, the sensor recalibrates itself. The process then ends at block 670.

Figure 7:
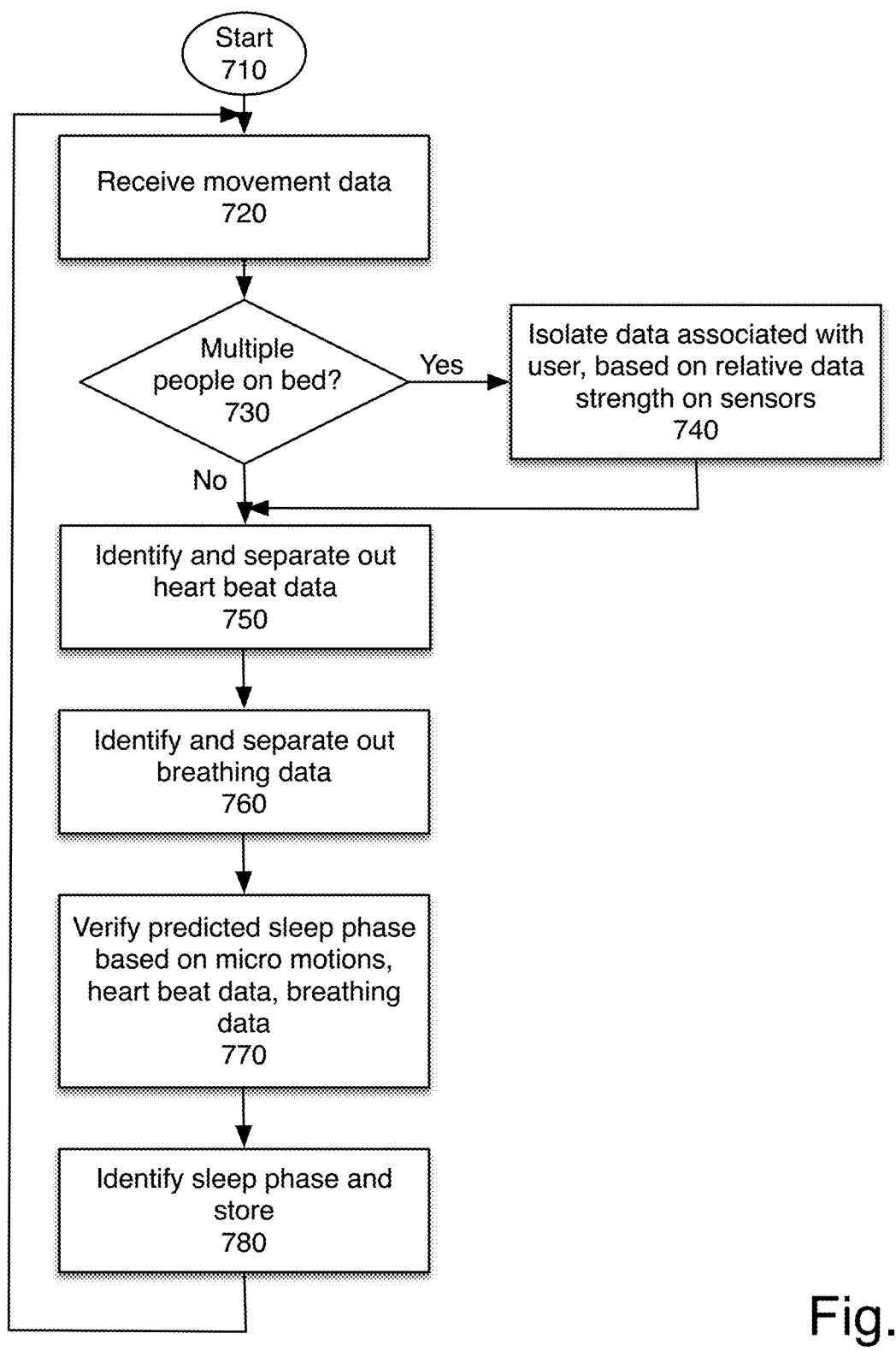
FIG. 7 is a flowchart of one embodiment of identifying sleep phase based on data from the sensor system.

FIG. 7 is a flowchart of one embodiment of identifying sleep phase based on data from the sensor system. The process starts at block 710. In one embodiment, this process runs continuously when the user is sleeping.

At block 720, the system receives movement data. In one embodiment, movement data is received from the inductive sensor. In one embodiment, movement data may also be received from additional sensors, such as a wristband, or mobile device. In one embodiment, data from multiple devices may be combined to generate the movement data.

At block 730, the process determines whether there are multiple people on the bed. When there are multiple people on the bed, the system must isolate data for each user, to be able to evaluate the user's sleep.

If there are multiple people on the bed, at block 740, the data is isolated, based on the relative data strength received from the sensors. As a general rule, each sensor will detect movement by anyone on the bed. However, the sensor in closer proximity to the user will sense a stronger movement from the same heart beat, breath, or micro motion. Therefore, the relative signal strength detected by multiple sensors may be used to isolate the data associated with each user. The process then continues to block 750.

At block 750, the heart beat data is isolated. Each heart beat moves the user's body slightly. The heart beat is the cardiac cycle, including diastole, systole, and intervening pause. Heart beats are generally at a particular frequency, called the heart rate. The heart rate slows during sleep but does not generally change quickly. Therefore, the heart beat data can be isolated based on the known heart rate, and the cardiac cycle information.

At block 760, the breathing data is separated out. Each breath inflates the user's lungs and thus causes motion in the mattress. Breathing is also rhythmic, and includes the contraction and flattening of the diaphragm, and the relaxation of the diaphragm. Breathing is generally slowed in deeper sleep, however the rhythmic pattern of breathing continues. This data is used to separate out breathing data.

Once breathing data and heart beat data are identified in the motion data, the remaining information is the micro-motions made by the user in sleep.

At block 770, the combination of micro-motion data, heart beat data, and breathing data is used to determine the user's sleep phase, or verify the predicted sleep phase. At block 780, the appropriate sleep phase is identified. The process then stores this data, and returns to block 720 to continue monitoring. In one embodiment, all of these data elements are stored, and may be used in later analysis to identify health conditions, sleep patterns, and potentially other facts that may impact the user's life or health. In one embodiment, because the sensors are very sensitive, even various issues such as hiccups or restless leg syndrome or sleep paralysis. In one embodiment, in addition to making this information available to the user, the system may also utilize this information to optimize the user's sleep quality.

Figure 8:
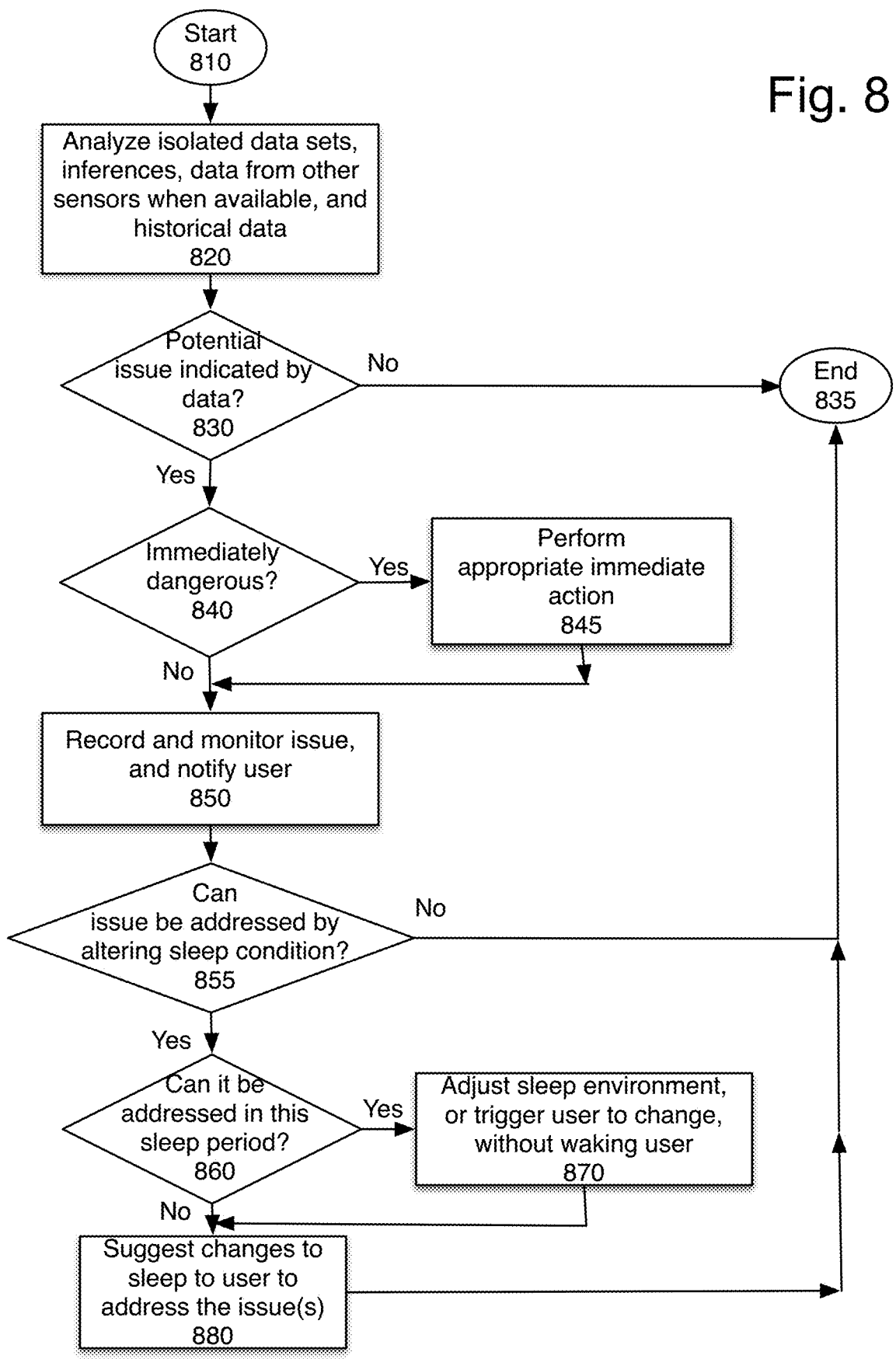
FIG. 8 is a flowchart of one embodiment of identifying potential health issues based on data from the sensor system.

FIG. 8 is a flowchart of one embodiment of identifying potential health issues based on data from the sensor system. The process starts at block 810. In one embodiment, the data obtained from the monitoring system provides information including movements, heart rates, breathing, apnea, snoring, twitching, asymmetry, and other data that may be used to identify health issues. In one embodiment, the system monitors the user continuously, for sleep phase, and also monitors for any health issues. In one embodiment, the system utilizes a combination of the sleep sensor, sleep analysis system, and mobile device to obtain data. For example, in one embodiment, the mobile device is used for recording sounds, which may be useful for identifying and/or analyzing snoring, coughing, scratching, apnea, or other conditions. In one embodiment, the sensor data from various sources is integrated to form a complete picture. In one embodiment, the analytics system may turn on the various supporting sensors, as needed. For example, the inductive sleep sensor system may be on, and when the detected movement of the breath indicates that the user may be snoring, the system turns on the recording, within the sensor system or in an associated mobile device, to record audio data. Similarly, other sensors may be switched into the loop.

At block 820, the isolated data sets, inferences, data from other sensors is analyzed, when available. The data sets, in one embodiment, include the heart beat data (which includes heart rate, and any arrhythmia or other deviations from the standard cardiac cycle), breathing data (which includes snoring, apnea, and other information derived from the movement data), motion data, and micro-movement data. The derived data includes sleep phase data, symmetry data which indicates the symmetry of movements, sleep cycle patterns, the time the user and other data derived from the above data sets. Additionally, the system may utilize environmental data in its analysis. This may include local data such as the angle of the bed, the light level, temperature, humidity, etc. The system further uses data over time, to analyze for changes in the user's sleeping patterns, and changes in breathing or heart measurements that may indicate a potential health condition. For example, if a user over time starts to develop a tremor, starts to have intermittent apnea, starts to sleep badly, this may be detected by the system.

In one embodiment, at block 830 the process determines whether there is any potential issue indicated by the data. If no potential issue is indicated, the process ends at block 835. This process continuously analyzes the data sets available, to identify actual and potential problems. In one embodiment, anonymized data is shared with the system. This may be used to identify precursor data which precedes, and indicates a later developing problem. For example, the system may determine based on a large sample set that people who stop being able to sleep horizontally tend to develop detectable apnea after some time. Because the system learns from the patterns observed, and correlates them over many users and many sleep sessions, such data can be identified.

If there is a potential issue, at block 840 the process determines whether the issue is immediately dangerous. For example, if the user is choking, or has severe enough apnea, or there is a heart arrhythmia that may indicate a heart attack, the system identifies the issue as immediately dangerous, in one embodiment. If so, at block 845, and immediate action is taken. In one embodiment, an immediate action may be an attempt to rouse the user. In one embodiment, an immediate action may be to alert a third party, such as another sleeper or 911. In one embodiment, the immediate action may be to wake another person in the house who could check on the user. The process then continues to block 850. If the identified issue is not immediately dangerous, the process continues directly to block 850.

At block 850, the data for the issue is recorded, and monitored. The user is informed, in one embodiment upon waking. In one embodiment, the data is made available to the user so that the user can forward the information to his or her doctor.

At block 855, the process determines whether the issue can be addressed—cured or improved—by altering a sleep condition. For example, certain congestion issues can be fixed by using a thicker pillow or adjusting the adjustable bed to elevate the user's head. Similarly, some early apnea issues can be avoided if the sleeper does not sleep on his or her back. If the issue can't be addressed, the process ends at block 835. In one embodiment, the user may be alerted to find another method of addressing the detected problem.

If the process could be addressed, at block 860, the process determines whether the issue can be addressed in this sleep period. In one embodiment, using the smart phone Internet of Things system, the system is capable of adjusting certain sleep conditions. Thus, in one embodiment, the system may be able to alleviate the user's issues by adjusting one or more aspects of the sleep environment. For example, the system may turn on an air filter, adjust the inline of the bed, turn on or off lights or sounds, open or close blinds or even windows or doors, etc. In one embodiment, the system may be able to use light, motion, and/or sound guide the user to a different sleep state, which may address a condition as well.

If the condition can be addressed, the sleep environment may be adjusted, or the user may be triggered to change, without waking the user, at block 870. In one embodiment, the process then continues to block 880. At block 880, changes are suggested to the user to address the identified issue(s). These suggestions may include changing the sleep environment, visiting a doctor, altering behaviors, such as increasing exercise or changing eating habits, etc. The process then ends, at block 835.

One of ordinary skill in the art will recognize that the processes described in the above flowcharts are conceptual representations of the operations used. The specific operations of the processes may not be performed in the order shown and described. For example and in one embodiment, the process is interrupt driven, rather than sequentially testing for various occurrences. In one embodiment, data is received or processed in a different order. The specific operations may not be performed in one continuous series of operations, and different specific operations may be performed in different embodiments. Additional operations may be performed, or some operations may be skipped. Furthermore, the processes could be implemented using several sub-processes, or as part of a larger macro process. For instance, in some embodiments, the processes shown in these flowcharts are performed by one or more software applications that execute on one or more computing devices.

Figure 9:
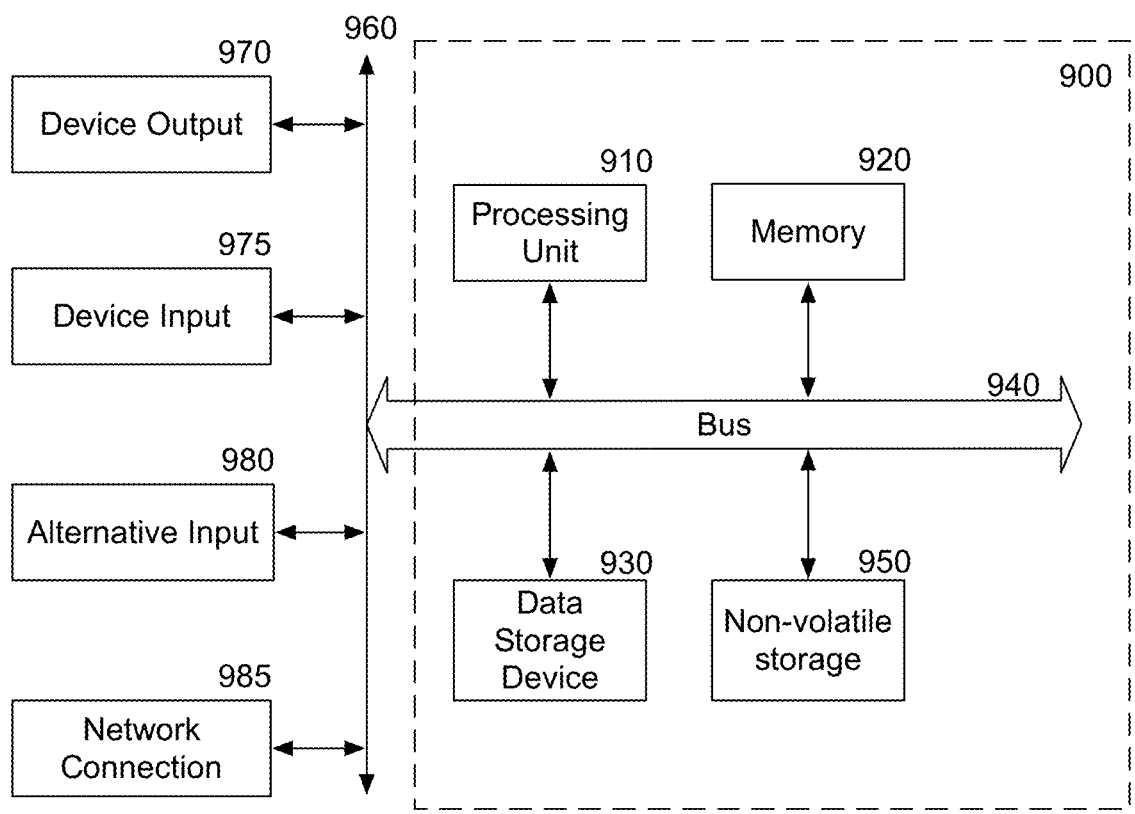
FIG. 9 is a block diagram of a computer system that may be used with the present invention.

FIG. 9 is a block diagram of one embodiment of a computer system that may be used with the present invention. It will be apparent to those of ordinary skill in the art, however that other alternative systems of various system architectures may also be used.

The data processing system illustrated in FIG. 9 includes a bus or other internal communication means 940 for communicating information, and a processing unit 910 coupled to the bus 940 for processing information. The processing unit 910 may be a central processing unit (CPU), a digital signal processor (DSP), or another type of processing unit 910.

The system further includes, in one embodiment, a random access memory (RAM) or other volatile storage device 920 (referred to as memory), coupled to bus 940 for storing information and instructions to be executed by processor 910. Main memory 920 may also be used for storing temporary variables or other intermediate information during execution of instructions by processing unit 910.

The system also comprises in one embodiment a read only memory (ROM) 950 and/or static storage device 950 coupled to bus 940 for storing static information and instructions for processor 910. In one embodiment, the system also includes a data storage device 930 such as a magnetic disk or optical disk and its corresponding disk drive, or Flash memory or other storage which is capable of storing data when no power is supplied to the system. Data storage device 930 in one embodiment is coupled to bus 940 for storing information and instructions.

The system may further be coupled to an output device 970, such as a cathode ray tube (CRT) or a liquid crystal display (LCD) coupled to bus 940 through bus 960 for outputting information. The output device 970 may be a visual output device, an audio output device, and/or tactile output device (e.g. vibrations, etc.)

An input device 975 may be coupled to the bus 960. The input device 975 may be an alphanumeric input device, such as a keyboard including alphanumeric and other keys, for enabling a user to communicate information and command selections to processing unit 910. An additional user input device 980 may further be included. One such user input device 980 is cursor control device 980, such as a mouse, a trackball, stylus, cursor direction keys, or touch screen, may be coupled to bus 940 through bus 960 for communicating direction information and command selections to processing unit 910, and for controlling movement on display device 970.

Another device, which may optionally be coupled to computer system 900, is a network device 985 for accessing other nodes of a distributed system via a network. The communication device 985 may include any of a number of commercially available networking peripheral devices such as those used for coupling to an Ethernet, token ring, Internet, or wide area network, personal area network, wireless network or other method of accessing other devices. The communication device 985 may further be a null-modem connection, or any other mechanism that provides connectivity between the computer system 900 and the outside world.

Note that any or all of the components of this system illustrated in FIG. 9 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 920, mass storage device 930, or other storage medium locally or remotely accessible to processor 910.

It will be apparent to those of ordinary skill in the art that the system, method, and process described herein can be implemented as software stored in main memory 920 or read only memory 950 and executed by processor 910. This control logic or software may also be resident on an article of manufacture comprising a computer readable medium having computer readable program code embodied therein and being readable by the mass storage device 930 and for causing the processor 910 to operate in accordance with the methods and teachings herein.

The present invention may also be embodied in a handheld or portable device containing a subset of the computer hardware components described above. For example, the handheld device may be configured to contain only the bus 940, the processor 910, and memory 950 and/or 920.

The handheld device may be configured to include a set of buttons or input signaling components with which a user may select from a set of available options. These could be considered input device#1 975 or input device#2 980. The handheld device may also be configured to include an output device 970 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 910, a data storage device 930, a bus 940, and memory 920, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 985.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 910. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

Figure 10:
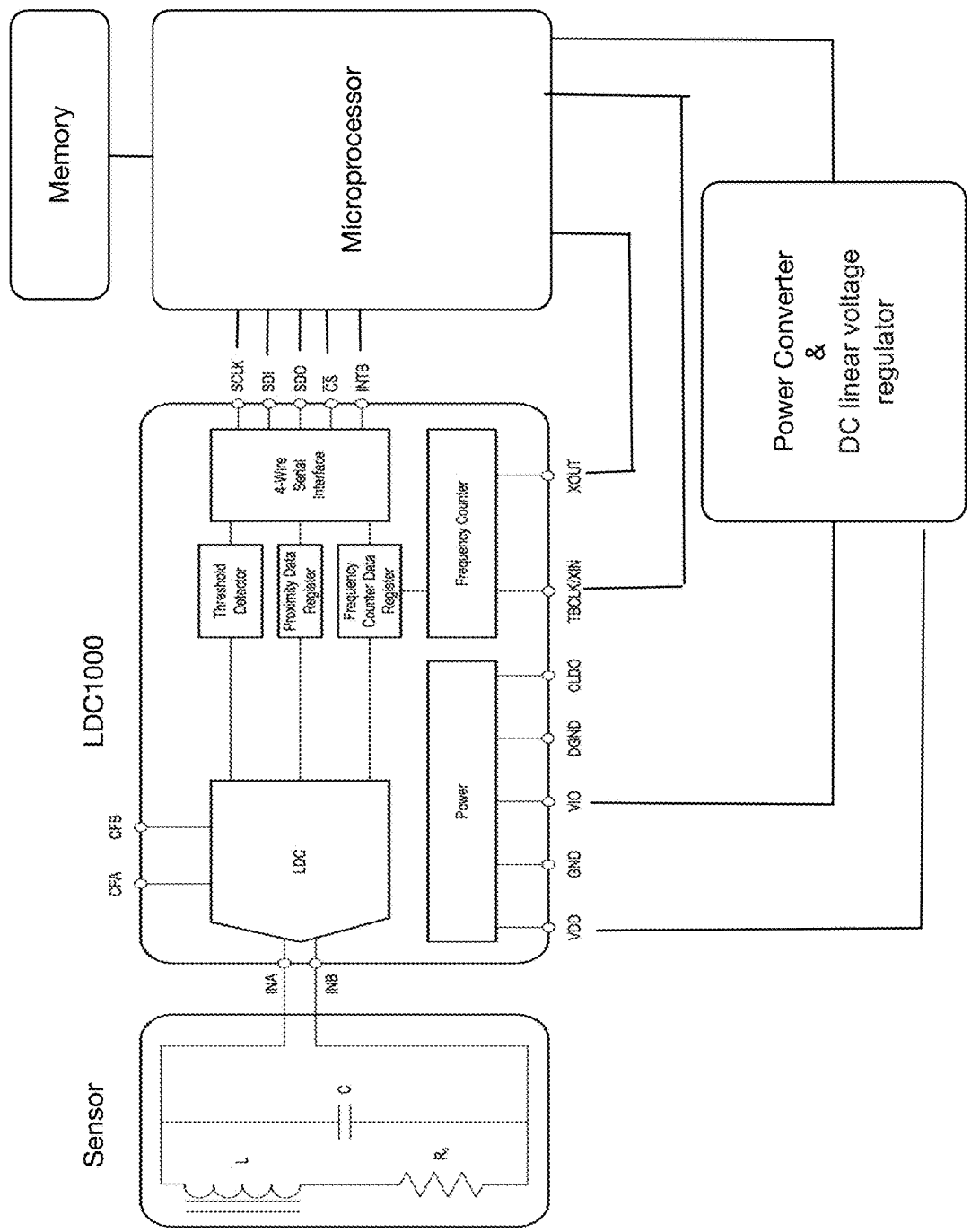
FIG. 10 is a circuit diagram of one embodiment of a sensor system that may be used with the present invention.

FIG. 10 is one embodiment of a circuit diagram of an inductive sensor system that may be used with the present invention. The sensor, in one embodiment, receives power from circuit LDC1000, and sends signal data back to LDC1000. The LDC1000 is coupled to a microprocessor, which includes either on-board or coupled memory to store data. Power converter provides power to LDC1000. In one embodiment, the power converter provides low power AC to the sensor as well as DC power to the microprocessor and circuit LDC1000. In one embodiment, the sensor and LDC1000 are placed into the box spring or mattress, while the microprocessor and power converter are coupled via a cable such as a CAT5 cable. In one embodiment, microprocessor, memory, and power converter are plugged into the wall, and provide processing of the data. In one embodiment, microprocessor may include a network connectivity capability. Alternatively, the network connection may be external to the microprocessor, but part of the sensor system.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A method comprising:
receiving data from one or more sleep sensors including an inductive sleep sensor, wherein the inductive sleep sensor comprises at least one fixed coil and a hinged metallic portion, the inductive sleep sensor integrated in a mattress system including a mattress and a solid base, wherein the at least one fixed coil of the inductive sleep sensor is directly attached to the solid base and the inductive sleep sensor measures force placed on the inductive sleep sensor by inductively sensing, by the at least one fixed coil, movement of the hinged metallic portion in a direction perpendicular to a sleep surface of the mattress system;
detecting two or more sleepers using the received data;
analyzing the received data to determine movements of the two or more sleepers on the mattress system, wherein analyzing the received data comprises:
monitoring relative data of the two or more sleepers; and
attributing a portion of the received data to a sleeper of the two or more sleepers using the relative data; and
providing results of the analyzed data to a user's mobile device via a wireless connection, for display to the user.

2. The method of claim 1, where the solid base of the mattress system comprises one or more of: a box spring, a bed frame, and slats supporting the mattress.

3. The method of claim 1, wherein the method further comprises isolating one or more physiological indicators including breathing, micromotion, and heart rate data from the received data and the determined movements and wherein the analyzing the received data is based on the one or more physiological indicators.

4. The method of claim 3, wherein the method further comprises determining a potential issue of the sleeper based on the received data and the determined movements and wherein providing results comprises notifying the user of the potential issue.

5. The method of claim 1, wherein the one or more sleep sensors comprise a plurality of separate sensor devices, each sensor device coupled to one or more other sensor devices.

6. The method of claim 5, wherein the plurality of separate sensor devices comprises two sensors, positioned at a head and a mid-chest height of the sleeper.

7. The method of claim 4, wherein the method further comprises:
  determining whether the potential issue can be addressed; and
  in response to determining that the potential issue can be addressed, adjusting a sleep environment of the sleeper based on the potential issue.

8. The method of claim 1, wherein the inductive sleep sensor is integrated into the solid base of an adjustable mattress foundation, the inductive sleep sensor coupled to a non-moving portion of the mattress foundation.

9. The method of claim 1, wherein the inductive sleep sensor is integrated into a slat supporting the mattress.

10. A sleep sensor system comprising:
  one or more sleep sensors including an inductive sleep sensor, wherein the inductive sleep sensor comprises at least one fixed coil and a hinged metallic portion, the inductive sleep sensor integrated in a mattress system, the mattress system including a mattress and a solid base, the at least one fixed coil of the inductive sleep sensor directly attached to the solid base, wherein the inductive sleep sensor measures force placed on the inductive sleep sensor by inductively sensing, by the at least one fixed coil, movement of the hinged metallic portion in a direction perpendicular to a sleep surface of the mattress system;
  data collection circuitry coupled to the inductive sleep sensor, wherein the data collection circuitry:
    receives data from the one or more sleep sensors;
    detects two or more sleepers using the received data;
    analyzes the received data to determine movements of the two or more sleepers on the mattress system, wherein analyzing the received data comprises:
      monitoring relative data of the two or more sleepers; and
      attributing a portion of the received data to a sleeper of the two or more sleepers using the relative data; and
  a wireless connection to provide results of the analyzed data to a user mobile device for display to the user.

11. The sleep sensor system of claim 10, wherein the solid base of the mattress system comprises one of a foundation, a slat, or a box spring.

12. The sleep sensor system of claim 10, further comprising:
  a sensor case having a top and a bottom compressible sides, and the hinged metallic portion, wherein movements of the sleeper move the hinged metallic portion of the sensor case which is inductively sensed by the inductive sleep sensor.

13. The sleep sensor system of claim 12, wherein the compressible sides do not compress completely when a sleeper is lying on the mattress, to enable movement due to micro-motions of the sleeper on the mattress.

14. The sleep sensor system of claim 12, wherein the compressible sides are foam.

15. The sleep sensor system of claim 10, further comprising:
  a sensor case having a top and a bottom, wherein the top is a curved top which moves due to motions of the sleeper.

16. The sleep sensor system of claim 10, wherein:
  the data collection circuitry further determines a potential issue of the sleeper based on the received data and the determined movements and wherein providing results comprises notifying the user of the potential issue.

17. The sleep sensor system of claim 16, further comprising:
  a sleep environment adjustor, wherein the data collection circuitry further determines whether the potential issue can be addressed and wherein the sleep environment adjustor, in response to determining that the potential issue can be addressed, adjusts a sleep environment of the sleeper based on the potential issue.

18. A sleep sensor system comprising:
  a mattress having a sleep surface to receive a sleeper;
  a solid base for the mattress, the solid base comprising one of: a box spring, a foundation, a slat, or a base completely beneath the mattress;
  an inductive sensor integrated into the solid base, wherein the inductive sleep sensor comprises at least one fixed coil and a hinged metallic portion, wherein the inductive sensor inductively detects micromovements of the sleeper, wherein the inductive sleep sensor measures force placed on the inductive sleep sensor by inductively sensing, by the at least one fixed coil, movement of the hinged metallic portion in a direction perpendicular to the sleep surface of the mattress;
  a data collection circuitry coupled to the inductive sleep sensor, wherein the data collection circuitry:
    receives data from one or more sleep sensors;
    detects two or more sleepers using the received data;
    analyzes the received data to determine movements of the two or more sleepers on the mattress system, wherein analyzing the received data comprises:
      monitoring relative data of the two or more sleepers; and
      attributing a portion of the received data to a sleeper of the two or more sleepers using the relative data; and
  a wireless connection to provide results of the analyzed data to a user mobile device for display to the user.

19. The sleep sensor system of claim 18, wherein the inductive sensor comprises an inductive sleep sensor comprising the at least one fixed coil in a sensor case comprising the hinged metallic portion.

20. The sleep sensor system of claim 19, wherein the sensor case is compressible and wherein detecting micromovements of the sleeper is based on inductively sensing the movement of the hinged metallic portion of the sensor case.

21. The sleep sensor system of claim 18, further comprising:
  a signal converter to convert data from the inductive sleep sensor to a digital signal, the digital signal sent via a cable to the data collection circuitry.

\* \* \* \* \*